United States Patent [19]

Kung et al.

[11] Patent Number: 5,006,459

[45] Date of Patent: Apr. 9, 1991

[54] THERAPEUTIC AND DIAGNOSTIC METHODS USING SOLUBLE T CELL SURFACE MOLECULES

[75] Inventors: Patrick C. Kung, Cambridge; Stephen Ip, Framingham; Michael Brown, Wayland, all of Mass.; Linda A. McKeen, Point Pleasant, Pa.

[73] Assignee: T Cell Sciences, Inc., Cambridge, Mass.

[21] Appl. No.: 20,819

[22] Filed: Mar. 2, 1987

Related U.S. Application Data

[63] Continuation-in-part of Ser. No. 846,230, Mar. 31, 1986, abandoned.

[51] Int. Cl.[5] .................. G01N 33/566; G01N 33/569; G01N 33/574; G01N 33/577
[52] U.S. Cl. ........................................ 435/5; 435/7.23; 435/810; 435/7.24; 435/975; 436/501; 436/506; 436/510; 436/518; 436/536; 436/548; 436/811; 436/813; 530/395; 530/806; 935/110
[58] Field of Search .............. 436/501, 506, 518, 536, 436/548, 811, 813, 510; 530/350, 395, 806; 935/110; 435/5, 7, 810

[56] References Cited

U.S. PATENT DOCUMENTS

4,376,110 3/1983 David et al. ................. 436/548
4,707,443 11/1987 Nelson et al. ................. 436/800

OTHER PUBLICATIONS

Fujimoto et al., *Journ. Exp. Med.*, 159, 752–766, 1983.
Fujimoto et al., *Journ. Exp. Med.*, 160, 116–124, 1984.
Greene et al., *Ann. Intern. Med.*, 105, 560–572, 1986.
MacKeen et al., *Fed. Proc.*, 45, p. 454, Abs. No. 1746 (1986).
Nelson, *Fed. Proc.*, 45, p. 377, Abs. No. 1294 (1986).
Rubin et al., *Clin. Res.*, 33, 457A, (1985).
Rubin et al., *Journ. Immunol.*, 135, 3172–3177 (1985).
Rubin et al., *Leukocytes and Most Defense*, Alan R. Liss, Inc., New York, 1986, pp. 95–102.
Snow et al., *Journ. Biol. chem.*, 260, 2700–2708, 1985.

Kung et al., *Science* 206:347–349 (1979).
Reinherz et al., *Proc. Natl. Acad. Sci. U.S.A.* 76:4061–4065 (1979).
Reinherz et al., *Proc. Natl. Acad. Sci. U.S.A.* 77:1588–1592 (1980).
Verbi et al., *Eur. J. Immunol.* 12:81–86 (1982).
Kanellopoulos et al., *The EMBO J.* 2:1807–1814 (1983).
Kung et al., *Int. J. of Dermatol.* 22:67–74 (1983).
Krensky and Clayberger, *Transplantation* 39:339–348 (1985).

(List continued on next page.)

*Primary Examiner*—Esther L. Kepplinger
*Assistant Examiner*—David A. Saunders
*Attorney, Agent, or Firm*—Pennie & Edmonds

[57] ABSTRACT

The present invention is directed to the measurement of soluble T cell growth factor receptors, soluble T cell differentiation antigens, or related soluble molecules or fragments thereof, and the use of such measurements in the diagnosis and therapy of diseases and disorders. The measurement of such molecules can be valuable in monitoring the effect of a therapeutic treatment on a subject, detecting and/or staging a disease in a subject, and in differential diagnosis of a physiological condition in a subject. These measurements can also aid in predicting therapeutic outcome and in evaluating and monitoring the immune status of patients.

In specific embodiments, measurements of serum or plasma interleukin-2 receptor levels can be made, to detect or stage leukemia or lymphoma. In other embodiments, IL2R levels, or CD8 levels, can be used to differentially diagnose renal allograft rejection, as distinguished from Cyclosporin A nephrotoxicity. In another embodiment, CD8 levels can be measured to differentially diagnose rheumatoid arthritis, as distinct from other joint diseases.

In particular embodiments, measurements of the soluble T cell surface molecules can be accomplished by sandwich enzyme immunuoassays.

31 Claims, 18 Drawing Sheets

OTHER PUBLICATIONS

McDougal et al., Science 231:382-385 (1986).
Miller et al., Blood 68(1):78-86 (1981).
Falcao et al., J. Clin. Lab. Immunol. 13:141-143 (1984).
Oh et al., Scan. J. Immunol. 22:51-60 (1985).
Acuto et al., Cell 34:717-726 (1983).
Brenner et al., J. Exp. Med. 160:541-551 (1984).
Meuer et al., Proc. Natl. Acad. Sci. U.S.A. 81:1509-1513 (1984a).
Meuer et al., Ann. Rev. Immunol. 2:23-50 (1984b).
McKenzie and Parish, J. Exp. Med. 144:847-851 (1976).
Parish et al., Immunogenetics 3:129-137 (1976).
Parish and McKenzie, Cellular Immunol. 33:134-144 (1977).
Parish et al., Infection and Immunity 26:422-426 (1979).
Wilson et al., J. Immunol. 122:1967-1971 (1979).
Sandrin et al., J.N.C.I. 66:279-283 (1981).
Mier and Gallo, Proc. Natl. Acad. Sci. U.S.A. 77:6134-6138 (1980).
Smith, Immunol. Rev. 51:337-357 (1980).
Arya et al., Science 223:1086-1087 (1984).
Lotze et al., J. Immunol. 135:2865-2875 (1985).
Touw et al., Blood 66:556-561 (1985).
Robb et al., J. Exp. Med. 154:1455-1474 (1981).
Uchiyama et al., J. Immunol. 126:1393-1397 (1981).
Leonard et al., Nature 300:267-269 (1982).
Korsmeyer et al., Proc. Natl. Acad. Sci. U.S.A. 80:4522-4526 (1983).
Depper et al., J. Immunol. 133:1691-1695 (1984).
Sugamura et al., Proc. Natl. Acad. Sci. U.S.A. 81:7441-7445 (1984).
Tsudo et al., J. Exp. Med. 160:612-617 (1984).
Waldmann et al., J. Exp. Med. 160:1450-1466 (1984).
Dower et al., J. Exp. Med. 162:501-515 (1985).
Ebert et al., Clin Immunol. and Immunopathol. 37:283-297 (1985).
Rubin et al., Hybridoma 4:91-102 (1985).
Uchiyama et al., J. Clin. Invest. 76:446-453 (1985).
Greene and Leonard, Ann. Rev. Immunol. 4:69-95 (1986).
Gupta, Clin. Immunol. and Immunopathol. 38:93-100 (1986).
Mutsuoka et al., Leukemia Res. 10:597-603 (1986).
Tsudo et al., Blood 67:316-321 (1986).
Tuow et al., Blood 68:1088-1094 (1986).
Chilosi et al., Int. J. Biological Markers 2:101-104 (1986).
Durno et al., Blood 68 Suppl. #1, 124a (1986).
John et al., Sixth Int. Cong. Immunol. Toronto, Canada (1986).
Keller et al., Am. Diabetes Assoc. (1986).
Nelson et al., Pediatric Res. 20:136-139 (1986).
Pizzolo et al., Blood 68 Suppl. #1, 228a (1986).
Reuben et al., Blood 68 Suppl. #1, 213a (1986).
Rubin et al., J. Immunol. 137:3841-3844 (1986).
Saadeh et al., Fed. Proc. 45:378 (1986).
Treiger et al., J. Immunol. 136:4099-4105 (1986).
van Es et al., Transplantation 37:65-69 (1984).
Austen and Cosimi, N. Engl. J. Med. 311:1436-1438 (1984).
Hancock et al., Transplantation 39:430-438 (1985).
Magrath et al., Blood 63:1102-1111 (1984).
Pui et al., Blood 66:778-782 (1985).
Murphy et al., J. Clin. Oncol. 4:1732-1739 (1986).
Arseneau et al., Am. J. Med. 58:314-321.

THERAPEUTIC AND DIAGNOSTIC METHODS USING SOLUBLE T CELL SURFACE MOLECULES

The present application is a continuation-in-part of copending application Ser. No. 846,230 filed Mar. 31, 1986, now abandoned, which is incorporated by reference herein in its entirety.

TABLE OF CONTENTS

1. Introduction
2. Background of the Invention
   2.1 T Cell Growth Factors and Receptors
   2.2. T Cell Surface Molecules
   2.3. Soluble Immune Cell Surface Molecules
3. Summary of the Invention
   3.1. Definitions
4. Description of the Figures
5. Detailed Description of the Invention
   5.1. Monitoring the Effect of a Therapeutic Treatment
   5.2. Detecting and/or Staging a Disease in a Subject
   5.3. Differential Diagnosis of a Physiological Condition
   5.4. Soluble T cell Growth Factor Receptors, T Cell Differentiation Antigens, and Related Molecules
      5.4.1. Assays for Measurement
6. Soluble IL2R Detection in Patients
   6.1. Monoclonal Antibodies
   6.2. Soluble IL2R Assay
      6.2.1. Procedure
      6.2.2. IL2R Control Standards
      6.2.3. Flow Cytometric Method
7. There is No Correlation Between Soluble IL2R Level and IL2R Bearing Lymphocytes In Vivo
8. Serum Measurement of Soluble IL2R May be Used for Staging Leukemia or Monitoring a Therapeutic Treatment
9. High Serum IL2R Levels are Related to Advanced Disease and a Poor Outcome in Childhood Non-Hodgkin's Lymphoma
   9.1.Patients and Methods
      9.1.1. Patients
      9.1.2. Treatment
      9.1.3. Determination of Soluble IL2R Levels
      9.1.4. Determination of Serum Lactic Dehydrogenase
      9.1.5. Statistical Analysis
   9.2. Results
      9.2.1. Soluble IL2R Levels Show a Clear Relationship to Disease Stage
      9.2.2. Soluble IL2R Levels show a Linear Relationship with Serum LDH Levels
      9.2.3. Higher Soluble IL2R Levels are Associated with a Poorer Treatment Outcome
10. Elevated Soluble IL-2 Receptor Level in Serum of Cancer Patients Under Therapeutic Treatment
    10.1. Serum IL2R Levels in Cancer Patients Treated with IL-2
    10.2. Elevated Serum IL2R Levels in Cancer Patients Who Respond to IL-2 Therapy
11. Serum Level of Soluble IL2R May be Used to Differentially Diagnose Between Transplant Rejection and Therapeutic Toxicity and to Monitor Therapeutic Toxicity
12. Plasma IL2R Levels in Renal Allograft Recipients
    12.1. Patients and Methods
    12.2. Plasma Contains Elevated Levels of Soluble IL2R During Episodes of Renal Allograft Rejection
13. A comparison of Serum IL2R Levels and Endomyocardial Biopsy Grades in the Monitoring of Cardiac Allograft Rejection
    13.1. Methods
    13.2. Normal IL2R Levels Indicate the Absence of Cardiac Allograft Rejection Whereas Elevated IL2R Levels Sstrongly Indicate Rejection
14. Serum Measurement of Soluble IL2R May be Used for Staging Viral Infections
15. CELLFREE ™ Enzyme Immunoassay for the Detection of Soluble, Released IL2R
    15.1. Principals of the Method
    15.2. CELLLFREE Test Kit Components and Suggestions
       15.2.1 Reagents Supplied
       15.2.2. Materials Required But Not Provided
       15.2.3. Reagents Precautions
       15.2.4. Specimen Collection and Handling
       15.2.5. Reagent Preparation
       15.2.6. Suggested Plate Coating Protocol
       15.2.7 Suggested Assay Protocol
       15.2.8. Construction of a Standard Curve p2 15.2.9. Patient Samples
       15.2.10. Limitations
    5.3. CELLFREE ™ Reagents
       15.3.1. Monoclonal Antibodies
       15.3.2. Standards
       15.3.3. Patient Sera
       15.3.4. Purified IL2R
       15.3.5. Interleukin-2
    15.4. CELLFREE ™ IL2R Assay
       15.4.1. Standardization
       15.4.2. Precision
       15.4.3. Accuracy
       15.4.4. Specificity of Assay and Effects of Interleukin-2
       15.4.5. IL2R Levels in Human Sera
16. Soluble IL-1 Receptor Detection in Patient Serum
    16.1. Monoclonal Antibodies
    16.2. Soluble IL-1 Receptor Assay
    16.3. Results
17. Soluble CD8 Detection in Patients
    17.1. Monoclonal Antibodies
    17.2. Soluble CD8 Assay
    17.3. CD8 Control Standards
    17.4 Enzyme Immunoassay for the Quantitation of Cell-Free Human T Cell CD8-Like Molecule
       17.4.1 Evaluation of Anti-CD8 Monoclonal Antibodies as a Capture Antibody
18. Serum CD8 Levels in Evaluation of Diseases and Disorders
    18.1. Differential Diagnosis of Rheumatoid Arthritis
    18.2. Serum CD8 Levels in a Renal Allograft Recipient
    18.3. Serum CD8 Levels in Children with Non-Hodgkin's Lymphoma
    18.4. CD8 Levels in Infectious Disease
19. Molecular Characterization of the Soluble CD8 Antigen
    19.1 Methods
    19.2. Anti-CD8 mAbs Recognize a Soluble CD8 Antigen of 52-55 Kilodaltons
20. Soluble CD2 Detection
21. Deposit of Hybridomas

1. INTRODUCTION

The present invention is directed to the measurement of soluble T cell surface molecules, such as soluble T cell growth factor receptors and T cell differentiation antigens or fragments thereof, and the application of such measurements in the diagnosis and therapy of diseases and disorders. The measurement of such molecules can be used in monitoring the effect of a therapeutic treatment, detecting and/or staging disease or in differential diagnosis of a physiological condition.

2. BACKGROUND OF THE INVENTION

2.1 T CELL GROWTH FACTORS AND RECEPTORS

T cells secrete a variety of polypeptides affecting immunoregulation of hematopoietic cells and are themselves subject to regulation by hormone peptides interacting with specific receptors on their cell surface Interleukin 2, originally termed T cell growth factor, is synthesized and secreted by antigen- or lectin-activated T lymphocytes in the presence of macrophage-derived interleukin-1 and must interact with specific high-affinity membrane receptors to exert its biological effects (Smith, K. A., 1980, Immunol. Rev. 51:337-357; Leonard, W. J., et al., 1983, Proc. Natl. Acad Sci. U.S.A. 80:6957-6961). The interleukin 2 receptor (IL2R, Tac antigen) is not present on the surface of resting T or B lymphocytes. Upon activation by specific antigens or mitogens, T cell proliferation is mediated by an autocrine mechanism whereby activated cells secrete interleukin 2 (IL-2) and also express cell surface receptors for IL-2 (IL2R) (Mier, J. W., and Gallo, R. C., 1980, Proc. Natl. Acad. Sci. U.S.A. 77:6134; Robb, R. J., et al., 1981, J. Exp. Med. 154:1455; Leonard, W. J., et al., 1982, Nature 300:267; Meuer, S. C., et al., 1984, Proc. Natl. Acad. Sci. U.S.A. 81:1509; Tsudo, M. et al., 1984, J. Exp. Med. 160:612-617; Waldmann, T. A., et al., 1984, J. Exp. Med 160: 1450-1466).

Interaction of IL-2 with its cell surface receptor results in a continuous T cell proliferation (Greene, W. C. K. A., 1984, Ann, Rev. Immunol. 2:319-333). Measurement of IL2R provides information on the state of immune activation of the lymphoid population. This has been accomplished by measuring IL2R on cell surfaces using flow cytometry or fluorescence microscopy. Using monoclonal antibodies which define the IL-2 receptor, altered IL-2 receptor expression has been reported in a number of immune abnormalities (Greene and Leonard, supra; Depper, J. M., et al., 1984, J. Immunol. 133:1691-1695). Membrane IL2R has been found on certain B- or T-cell malignancies including Burkitt's lymphoma (Waldmann, T. A., et al., 1984, J. Exp. Med. 160:1450-1466), hairy cell leukemia (Waldmann et al., supra; Korsmeyer, S. J., et al., 1983, Proc. Natl. Acad. Sci. U S.A. 80:4522-4526), and human T cell leukemia virus (HTLV)-I-associated adult T cell leukemia (Depper, J. M., et al., 1984, J. Immunol. 133:1691-1695). The function of 25 cellular IL2R in lymphoid malignancies has not been fully elucidated. Several cases of common, pre-B or T cell acute lymphoblastic leukemia (ALL) have been induced to express IL2R after in vitro activation (Touw, I., et al., 1985, Blood 66:556-561; Touw, I., et al , 1986, Blood 68:1088-1094; Matsuoka, M., et al., 1986, Leuk. Res. 10:597-603) and, in some cases, interleukin 2 stimulated subsequent colony formation of neoplastic progenitor cells in vitro (Touw, 1985, supra; Touw, 1986, supra).

Leukemia cells from some patients with T cell chronic lymphocytic leukemia were shown to have the receptors and a good proliferative response to exogenous interleukin 2 (Uchiyama, T., et al., 1985, J. Clin. Invest. 76:446-453; Tsudo, M., 1986, Blood 67:316-321). However, HTLV-1 associated adult T cell leukemia constitutively expressed high levels of cell surface IL2R but had no or very poor proliferative responses to interleukin 2 (Uchiyama, 1985, supra; Arya, S. K., et al., 1984, Science 223:1086-1087). Ebert et al. (1985, Clin. Immunol. Immunopathol 37:283-297) have reported that T cells from patients with AIDS virus lack the ability to express IL2R on their surface even when the cell is activated.

Secondary signals in T cell activation such as interleukin-1 (IL-1) are provided by monocytes or other accessory cells, and are required for IL-2 secretion (Schmidtke, J. R., and Hatfield, S., 1976, J. Immunol. 116:357; Maizel, A. L., et al., 1981, J. Exp Med. 153:470; Williams, J. M., et al., 1985, J. Immunol 135:2249).

2.2. T CELL SURFACE MOLECULES

Clusters of differentiation (CD) have been established which define human leukocyte differentiation antigens (Bernard and Boumsell, 1984, Hum. Immunol 11:1-10), by the comparison of reactivities of monoclonal antibodies directed against the differentiation antigens. The T cell surface antigens, their classification into epitope-defined subgroups, and their distributions on T cells have been studied by use of monoclonal antibodies directed against human T cells (Clark et al., 1983, Immunogenetics 18:599-615; Hansen et al., 1984, in Leucocyte Typing, Bernard, A., et al., eds., Springer-Verlag, New York, pp. 195-212). Some of the T cell clusters of differentiation and other T cell surface molecules are listed in Table I.

TABLE I

| T CELL SURFACE MARKERS | | | | |
|---|---|---|---|---|
| T Cell Surface Marker | Molecular Weight (kd) | Expression | Detection Monoclonal Antibody | Reference |
| T Cell Antigen Receptor | 90 | All T Cells | T40/25 | Brenner, M. B., et al., 1984, J. Exp. Med. 160: 541-551 |
| CD8 | 30/43 | Suppressor/ cytotoxic (subset of T cells) | OKT8 Leu 2 | Reinherz, E. L., et al., 1979, PNAS USA 76:4061-4065; Ledbetter, J. A., et al., 1981 Monoclonal Antibodies and T Cell Hybridoma Elsevier/ |

TABLE I-continued
T CELL SURFACE MARKERS

| T Cell Surface Marker | Molecular Weight (kd) | Expression | Detection Monoclonal Antibody | Reference |
|---|---|---|---|---|
| T6 | 49 | Thymocytes & Langerhans Cells Leukemia Cells | OKT6 NAI/34 | North Holland, N. Y., pp. 16–22. Reinherz, 1979, supra. |
| CD4 | 62 | Helper/Inducer Cells (subset of T cells) | OK4 Leu 3a | Kung, P. C., et al., 1979, Science 206: 347–349 |
| CD3 | 19 | Pan T Cell | OKT3 | Kung, id. |
| TAC | 50 | IL-2 Receptor (Activated T Cells) | Anti-TAC | Uchiyawa, T., et al., 1981, J. Immunol. 126(4):1393–1397 |
| T9 | 94 | Transferrin Receptor (Activated T Cells) | OKT9 | Reinherz, E. L., et al., 1980, PNAS USA 77:1588–1592 |
| CD2 | 50 | All T Cells | OKT11 Leu 5 | Verbi, W., et al., 1982, Eur. J. Immunol. 12:81–86 |
| VLA-1 | 130/165/210 | Late Activated T Cells | VLA-1 | Helmer, M. E., et al., 1984, J. Immunol. 132:3011–3018 |

These T cell surface markers serve as markers of the cell lineage, the identity of the functional T cell subset to which the T cell belongs, and the activation state of the T cell. Several of the cell surface molecules have been studied in great detail and have been found to be important in initiating and regulating immune functions, and are critical to communication processes between immune cells. T cell antigen receptor, a surface molecule which comprises a disulfide-linker dimer of approximately 90 kilodaltons (kd), recognizes specific antigens and is responsible for initiating a complex series of biochemical events which constitute the T cell activation process (Meuer, S. C., et al., 1984, Ann. Rev. Immunol. 2:23–50; Acuto, O., et al., 1983, Cell 34:717–726). The CD3 structure is a three-chain complex associated with the T cell receptor (Kannellopoulos, J. M., et al., 1983, EMBO J. 2:1807; Borst, J., et al., 1983, Eur. J. Immunol 13:576; Van Den Elsen, P, et al., 1984, Nature 312:413; Meuer, SIC., et al., 1983, J. Exp. Med. 157:705). Lymphokine receptors, e.g. interleukin 2 (IL-2) receptor and interleukin 1 (IL-1) receptor, are essential for the activation and proliferation of T cells (Smith, K. A., 1984, Ann. Rev. Immunol. 2:319–333; Dower, S. K., et al., 1985, J. Exp. Med. 162:501–515). CD8 is a T cell specific surface molecule expressed on the surface of approximately 30% of T lymphocytes and is associated with suppression and cytotoxic functions. CD4 (OKT4 antigen) is expressed on the surface of approximately 60% of all T lymphocytes and is associated with helper function (Reinherz et al., 1979, Proc. Natl. Acad. Sci. U.S.A. 76:4061–4065). CD4 has also been identified as the receptor for the HTLV-III virus associated with acquired immune deficiency syndrome (AIDS) (McDougal, J. S., et al., 1986, Science 231:382–385). These various cell surface markers have enormous clinical application potentials for the identification of lymphocyte populations and their functional status (Krensky, A. M. and Clayberger, C., 1985, Transplant. 39(4):339–348; Kung, P. C., et al., 1984, Monoclonal Antibodies in Clinical Investigations, Clinical Biochemistry-Contemporary Theories and Techniques, vol. 3, Academic Press, pp. 89–115; Kung, P. C., et al., 1983, Int. J. Dermatol. 22(2):67–73).

Existing clinical methods of T cell typing involve the use of monoclonal antibodies which define T cell surface markers to detect the presence of specific cell surface markers on the T cell surface. Measuring the total numbers of T cells by surface markers has been useful for the characterization and classification of lymphoid malignancies (Greaves, M., et al., 1981, Int. J. Immunopharmac. 3(3):283–300). Changes in the relative percentage of T helper and T suppressor/cytotoxic cells were found to be associated with immune events in renal transplantation due to viral infection (Colvin, R. B, et al., 1981, Proc. 8th Int. Congr. Nephrol., Athens, pp. 990–996), autoimmune diseases (Veys, E. M., et al., 1981, Int. J. Immunopharmac. (3):313–319), and AIDS (Gupta, S., 1986, Clin. Immunol. Immunopathol. 38:93–100; Ebert, E. C., et al., 1985, Clin. Immunol. Immunopathol 37:283–297).

The expression of T cell surface markers has also been used for the assessment of the immune status of patients. It has been established that by measuring the relative number of distinct, functional T cell subsets, and/or the relative number of activated T cells in peripheral blood or tissues, an assessment of the immunological condition of a patient is possible. The activation antigens (e.g. IL-2 receptor) appear to be involved in T cell growth and differentiation processes.

2.3. SOLUBLE IMMUNE CELL SURFACE MOLECULES

Several immune cell surface markers have been detected in the serum. The molecules of the human major histocompatability complex (HLA molecules) are sets of cell surface glycoproteins involved in immune recognition. These macromolecular antigens have also been found to be present in body fluids such as serum (Pellegrino, M. A., et al., 1984, Meth. Enzymol. 108:614–624). The serum levels of Class I HLA-A and HLA-B have been shown to be present in sufficient quantity to perform HLA-typing in sera (Russo, C., et al., 1983, Transplant. Proc. 15(1):66-68; Pellegrino, M. A., et al., 1981, Transplant. Proc. 13(4):1935-1938). The presence of Class II HLA-DR in serum has also been detected (Sandrin, M. S., et al., 1981, J. Natl. Cancer Inst. 66(2) 279-283; Russo, C., et al., 1983, Transplant. Proc. 15(1):57-59)- The serum HLA-DR (Ia) has been shown to be markedly depressed in tumor patients. However, since HLA molecules are present in many cell types, their usefulness for disease diagnosis is limited.

Using monoclonal antibodies directed against different epitopes of human IL2R, Rubin et al., (1985, J. Immunol. 135:3172-3177; 1985, Fed. Proc. 44:946) detected a soluble form of IL2R that is released by activated normal peripheral blood mononuclear cells and synthesized in large amounts in vitro by HTLV-I-infected leukemic cell lines. A sandwich enzyme immunoassay was used to quantitate the soluble IL2R. The soluble immunoreactive molecules are somewhat smaller than the 55-65 kilodalton cell surface form of IL2R, and may be either a proteolytically released form or possibly a secreted species lacking the transmembrane portion (Treiger, B. F., et al., 1986, J. Immunol. 136:4099). Little is known about the functional significance of soluble IL2R. Since soluble IL2R is capable of binding interleukin 2 (Rubin, L. A., et al., 1985, supra), it may have an immunoregulatory role by competing with cellular IL2R for the ligand and thus down-regulating the immune response. In this regard, the soluble IL2R has been suggested to be a "blocking factor" produced by the malignant cells to inhibit the host's immune response to the tumor (Rubin, L. A., et al., 1985, supra; Greene, W. C., et al., 1986, Ann. Intern. Med. 105:560-572). Children with otitis media have also been found to have elevated soluble IL2R levels compared to those reported for healthy adults (Greene, W. C., et al., 1986, supra). Subsequent studies have disclosed comparable levels of soluble IL2R in cord blood and peripheral blood from normal adults (Greene, W. C., et al., 1986, Ann. Intern. Med. 105:560-572; Nelson, D. L., et al., 1986, Pediatr. Res. 20:136-139). Increased serum levels of IL2R have been found in patients with certain B or T cell malignancies, including HTLV-I-associated adult T cell leukemia, Sezary syndrome, Hodgkin's disease, chronic lymphocytic leukemia, hairy cell leukemia, and T cell lymphoma (Greene, W. C., 1986, supra; Nelson, D. C., 1986, Fed. Proc. 45:377; Saadeh, C., et al., 1986, Fed. Proc. 45:378; MacKeen, L., et al., 1986, Fed. Proc. 45:454; Rubin, L. A., et al., 1986, in Leukocytes and Host Defense, Oppenheim, J. J., and D. M. Jacobs, eds., Alan R. Liss, Inc., New York, pp. 95-102). Elevated levels of soluble IL2R have also been reported present in the serum of aged subjects (Saadeh, C., et al., 1986, supra), in patients with AIDS (id.) and in other clinical conditions characterized by increased T cell activation in vivo such as rheumatoid arthritis and lupus erythematosus (Nelson, D. L., 1986, Fed. Proc. 45:377; MacKeen, L., et al., 1986, Fed. Proc. 45:454). Applicants are also aware of the pending U.S. patent application, U.S. Ser. No. 724,897 filed Apr. 19, 1985, in the name of David Nelson et al., assigned to the U.S. Government and entitled "Soluble Interleukin-2 Receptor As An Indicator and Method of Assaying the Same." This patent application, which includes identical data to that of Rubin et al., (1985, J. Immunol. 135(5):3172-3177), concerns a soluble IL-2 receptor assay and purports to describe methods for diagnosing and monitoring diseases.

However, Rubin et al. (id.) do not teach or suggest methods for monitoring the effect of a therapeutic treatment, methods for assessing the degree of severity of a disease according to established classifications, or methods for differentially diagnosing a disease or condition from among two or more suggested diseases or conditions. Furthermore, U.S. Ser. No. 724,987 does not enable one skilled in the art to monitor the effects of a therapeutic treatment, to assess the severity of a disease, or to differentially diagnose a disease or condition from among two or more suspected diseases or conditions.

Several other cell surface markers which are primarily present on T cells have also been found in soluble form. CD2, a T cell surface molecule present in all normal T cells and a receptor for sheep red blood cells, has been detected at higher levels in the sera of certain cancer patients than those found in normal control patients (Falcao, R. P., et al., 1984, Clin. Lab. Immunol. 13:141-143; Oh. S.-K., et al., 1985, Scand. J. Immunol. 22:51-60). CD8 (Leu 2, OKT8), a surface marker found on the surface of suppressor/cytotoxic T cells and which may be involved in cellular recognition, has also been reported at highly elevated levels in the serum of patients with T cell leukemia (Fujimoto, J., et al., 1983, J. Exp. Med. 159:752-766). Leu-1, another T cell surface molecule, was measured in serum following anti-Leu-1 monoclonal antibody treatment (Miller, R. A., et al., 1982, New Engl. J. Med. 306:517-520). Oh et al. (1985, supra) reported that less than half of the patients with malignancies in their study presented elevated levels of soluble OKTII receptor in their serum.

However, not all T cell surface molecules are released into the serum (Fujimoto, J., et al., 1983, J. Exp. Med. 159:752-766). Leu 1 antigen was not detectable in the serum of normal or leukemic patients who have not received antibody therapy. Leu 3 antigens were also not detectable in soluble form in T cell culture supernatants (id.).

Additionally, coassigned, pending U.S. patent application, U.S. Ser. No. 804,289, filed Dec. 3, 1985, entitled "Assay Systems for Detecting Cell Free T Cell Antigen Receptor Related Molecules and Clinical Utilities of the Assays" concerns methods for diagnosing diseases and for monitoring diseased conditions by measuring the amount of soluble T cell antigen receptor in a subject's body fluid.

In sum, no known methods exist for utilizing the measured levels of soluble markers which are not disease specific in conjunction with other tests for monitoring the immune status of patients in response to a therapeutic treatment, staging the severity of a disease, or differentially diagnosing a disease or condition from among a multiplicity of diseases or conditions.

3. SUMMARY OF THE INVENTION

The present invention is directed to the measurement of soluble T cell growth factor receptors, soluble T cell differentiation antigens, or related soluble molecules or fragments thereof, and the use of such measurements in the diagnosis and therapy of diseases and disorders. The measurement of such molecules can be valuable in monitoring the effect of a therapeutic treatment on a subject, detecting and/or staging a disease in a subject, and in differential diagnosis of a physiological condition in a subject. These measurements can also aid in predicting therapeutic outcome and in evaluating and monitoring the immune status of patients.

In specific embodiments, measurements of serum or plasma interleukin-2 receptor levels can be made, to detect or stage leukemia or lymphoma. In other embodiments, IL2R levels, or CD8 levels, can be used to differentially diagnose renal allograft rejection, as distinguished from Cyclosporin A nephrotoxicity. In another embodiment, CD8 levels can be measured to differentially diagnose rheumatoid arthritis, as distinct from other joint diseases.

In particular embodiments, measurements of the soluble T cell surface molecules can be accomplished by sandwich enzyme immunoassays.

3.1. DEFINITIONS

As used herein, the following abbreviations will have the meanings indicated:

Staging a disease = assessing the degree of severity according to standard classifications
IL-2 = interleukin-2
IL-1 = interleukin-1
IL2R = interleukin-2 receptor
mAb = monoclonal antibody
NHL = non-Hodgkin's lymphoma
B-cell ALL = B-cell acute lymphoblastic leukemia
HTLV III/LAV/HIV = Human T Cell Leukemia Virus Type I/Lymphadenopathy Associated Virus/Human Immunodeficiency Virus
PHA = phytohemagglutinin
PBMC = peripheral blood mononuclear cell

4. DESCRIPTION OF THE FIGURES

FIG. 1. In vitro experiments in T cell activation. FIG. 1A: plot of concentration of soluble IL2R assayed in culture supernatants, cell lysates or cell surface of PHA stimulated human peripheral blood cells in culture. FIG. 1B: plot of concentration of soluble IL2R versus the percentage of activated T cells in culture.

FIG. 2. Soluble (serum) IL-2 receptor versus cell surface IL-2 receptor in vivo.

FIG. 3. Monitoring therapeutic treatment in cancer patients. Patient serum concentration of soluble IL2R is plotted against time. Time periods of active disease, treatment and remission are indicated.

FIG. 4. Distribution of serum interleukin-2 receptor (IL2R) levels among children with otitis media (OM); stage I or II non-Hodgkin's lymphomas (NHL); stage III or IV lymphoblastic (LB) NHL; stage III or IV diffuse small noncleaved-cell (SNC) NHL; and B-cell acute lymphoblastic leukemia (B-ALL). The dashed line separates IL2R values above or below 1000 U/ml.

FIG. 5. Comparison of log serum interleukin-2 receptor (IL2R) levels and log serum lactic dehydrogenase (LDH) levels. The straight line represents the least-squares regression fit to the data.

FIG. 6. Comparison of time-to-failure rates according to serum interleukin-2 receptor levels (IL2R) for (A) all patients with non-Hodgkin's lymphoma and B-cell acute lymphoblastic leukemia; (B) patients with stage III or IV non-Hodgkin's lymphoma or B-cell acute lymphoblastic leukemia. Significantly worse treatment results were evident for patients with higher levels (greater than 1000 U/ml) in both comparisons.

FIG. 7. Level of soluble (serum) IL-2 receptor in samples obtained from patients undergoing therapeutic treatment with IL-2.

FIG. 8. Serum IL2R levels in patients with lung carcinoma receiving IL-2 therapy. All patients were infused continuously from day 0 to 14 with recombinant IL-2. Patients 1 and 2 received $3 \times 10^6$ U/ml whereas patients 3, 4 and 5 received $2 \times 10^6$ U/ml.

FIG. 9. Transplantation monitoring and differential diagnosis of immune-rejection from Cyclosporin A toxicity (△-----△ = patients with rejection; ○---○ = patients with CsA toxicity; ●----● = stable renal transplant patients).

FIG. 10. Scatter plot of serum IL2R measurements (open triangles) versus histological grade of corresponding endomyocardial biopsy with superimposed non-linear regression plot (dashed curve). The equation for the regression is shown in the upper left of the plot below the linear correlation coefficient (R). EXP = exponent, BG = biopsy grade.

FIG. 11. Graph for patient A shows serum IL2R levels (open triangles) and biopsy grade (open squares) versus time for Patient A who has had an uneventful post transplant course. The patient was treated with additional steroids because of clinical signs of early rejection. Plot of data for Patient B shows correlations of IL2R levels and biopsy grade. This patient was transplanted during an episode of recurrent myocarditis perhaps resulting in the initial high value of IL2R. During rejection therapy with additional steroids, the biopsy grade remained at 2.0 (resolving rejection) but the IL2R fell to normal, i.e. below 545 units/mL. On day 60 post transplant, the biopsy grade fell to 1.0 but the IL2R level rose while the patient was receiving ATG. The biopsy grade 11 days later was 2.5 and the IL2R level was 2298 units/mL indicating recurrent rejection. S-M = Solumedrol. ATG = anti-thymocyte globulin, OKT-3 = Orthoclone OKT3.

FIG. 12. Staging of viral infection. Plot of serum levels of soluble IL2R of AIDS patients clinically diagnosed as indicated.

FIG. 13. Typical standard curve for measurement of soluble IL2R using the CELLFREE TM assay.

FIG. 14. Effects of addition of recombinant IL-2 on the CELLFREE TM serum assay kit performance.

FIG. 15. Levels of serum IL2R in normal healthy donor and patients with diseases as measured using the IL2R CELLFREE TM assay.

FIG. 16. Distribution of CD8 levels in serum and synovial fluids among patients with rheumatoid arthritis (RA), degenerative joint disease (DJ) and unclassified joint disease (UJ).

FIG. 17. Monitoring of a renal transplantation patient for serum CD8 and serum IL2R. Serum levels of either soluble IL2R or soluble CD8 are plotted against time. Episodes of CsA toxicity and rejection are indicated.

FIG. 18. Distribution of serum CD8 levels in children which non Hodgkins lymphoma (NHL) and acute lymphoblastic leukemia (ALL).

FIG. 19. Distribution of serum CD8 levels in patients with infectious disease.

DETAILED DESCRIPTION OF THE INVENTION

Figure 1B:
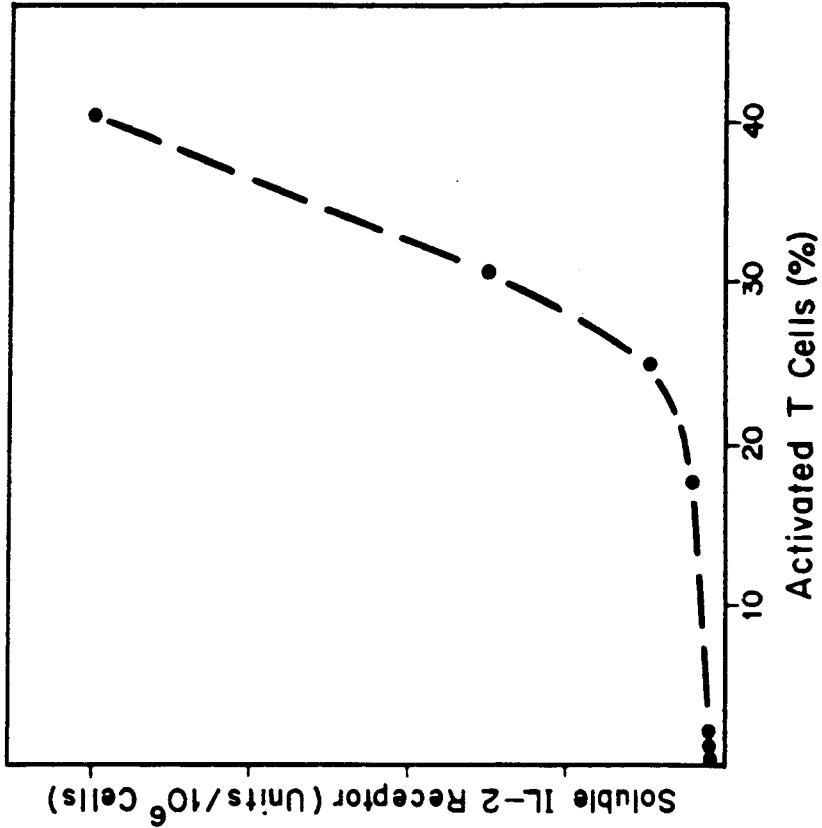

The present invention is directed to the measurement of soluble T cell growth factor receptors, soluble T cell differentiation antigens, or related soluble molecules or fragments thereof, and the use of such measurements in the diagnosis and therapy of diseases and disorders. The measurement of such molecules can be valuable in monitoring the effect of a therapeutic treatment on a subject, detecting and/or staging a disease in a subject, and in differential diagnosis of a physiological condition in a subject. These measurements can also aid in predicting therapeutic outcome and in evaluating and monitoring the immune status of patients The soluble molecule can be measured in any body fluid of the subject including but not limited to serum, plasma, urine, and saliva.

Proteinaceous macromolecules, or fragments thereof, derived from the surface of T cells, and proteinaceous macromolecules which have immunologically similar counterparts present on the surface of T cells or activated T cells, which are present in a body fluid and not associated with the surface of a T cell shall be herein referred to as soluble T cell surface molecules. These macromolecules can be either glycosylated or nonglycosylated and may be soluble by themselves or considered soluble by virtue of their association with other soluble macromolecules. Furthermore, macromolecules which are present in a fluid and are not bound to or associated with the surface of a cell are referred to as soluble macromolecules.

5.1. MONITORING THE EFFECT OF A THERAPEUTIC TREATMENT

The present invention provides a method for monitoring the effect of a therapeutic treatment on a subject who has undergone the therapeutic treatment. This method comprises measuring at suitable time intervals the amount of a soluble molecule or soluble fragment thereof which comprises, or is immunologically related to, a T cell growth factor receptor or T cell differentiation antigen. Any change or absence of change in the amount of the soluble molecule can be identified and correlated with the effect of the therapeutic treatment on the subject In a specific embodiment of the invention, soluble molecules immunologically related to the interleukin-2 receptor (IL2R) can be measured in the serum of patients by a sandwich enzyme immunoassay (for an example, see Section 15, infra), in order to evaluate the therapeutic efficacy of, for example, administration of immunomodulators such as alpha-interferon, Cyclosporin A, and monoclonal antibody OKT3. In another embodiment, soluble molecules related to the interleukin-1 receptor can be measured.

The therapeutic treatments which may be evaluated according to the present invention include but are not limited to radiotherapy, drug administration, immunosuppressive or immunoenhancive regimens, etc. The immunosuppressant regimens include, but are not limited to administration of drugs such as Cyclosporin A, chlorambucil, cyclophosphamide, or azathioprine, and anti-T cell antibody such as anti-T3 monoclonal antibody and anti-thymocyte globulin, etc. The immunoenhancive regimens include, but are not limited to administration of interleukin-1, interleukin-2, and other T cell growth factors

5.2. DETECTING AND/OR STAGING A DISEASE IN A SUBJECT

In another embodiment of the present invention, measurement of a soluble molecule which comprises, or is immunologically related to, a T cell growth factor receptor or T cell differentiation antigen can be used to detect and/or stage a disease or disorder in a subject. The measured amount of the soluble molecule is compared to standard amounts which are established to be normally present in the body fluid of subjects with various degrees of the disease or disorder. An amount present in the body fluid of the subject which is similar to a standard amount, established to be normally present in the body fluid of the subject during a specific stage of the disease or disorder, is indicative of the stage of the disease in the subject. Diseases or disorders which may be detected and/or staged in a subject according to the present invention include but are not limited to those listed in Table II, infra.

TABLE II

| DISEASES AND DISORDERS WHICH MAY BE DETECTED AND/OR STAGED IN A SUBJECT ACCORDING TO THE PRESENT INVENTION |
|---|
| I. Infectious Diseases<br>   Induced by virus:<br>     Herpesvirus<br>     Cytomegalovirus<br>     Epstein-Barr Virus<br>     HTLV-I<br>     HTLV-III/LAV/HIV (AIDS)<br>II. Cancer<br>   T cell leukemia<br>   HTLV-I-associated adult T cell leukemia<br>   T cell lymphoma<br>   Burkitt's lymphoma<br>   Hairy cell leukemia<br>   Sezary syndrome<br>   Hodgkin's disease<br>   Chronic lymphocytic leukemia<br>   Non-Hodgkin's lymphoma<br>   B-cell acute lymphoblastic leukemia<br>   Solid tumors<br>III. Autoimmune Diseases<br>   Rheumatoid arthritis<br>   Diabetes<br>   Multiple sclerosis<br>   Systemic lupus erythematosis<br>IV. Organ Allograft Rejection |

In specific embodiments of this aspect of the invention, measurements of plasma or serum levels of the IL2R or related molecules can be used in the detection of disease, or to determine disease stage and assign risk. For example, patients with lymphatic diseases and cancer such as non-Hodgkin's lymphoma or B cell acute lymphoblastic leukemia, or adult T cell leukemia can be monitored by measuring serum levels of soluble IL2R; elevated serum IL2R correlates directly with severity of the disease condition and indicates a poor response to therapy as well as a poor prognosis. In another example, the response of patients with non-lymphatic cancers to therapy with IL-2 can be monitored; in this case elevated serum levels of soluble IL2R indicates a positive response to IL-2 therapy. Responses to viral infections can also be monitored by measuring soluble IL2R levels in a patient. For example, patients infected with herpes virus or an AIDS virus present elevated serum levels of soluble IL2R. In another embodiment, plasma or serum IL2R levels can be measured in transplant patients; elevated serum levels of soluble IL2R is a diagnostic indication of allograft rejection. In another specific embodiment, T cell CD8-like molecules may be measured; detection of increased levels of soluble CD8 is associated with various diseases and disorders such as rheumatoid arthritis. Detection of elevated levels of a CD8-like antigen can indicate the involvement of significant numbers of suppressor/cytotoxic T cells with a specific pathological event, distinct from immune activation as measured by a rise in cell-free IL2R.

5.3. DIFFERENTIAL DIAGNOSIS OF A PHYSIOLOGICAL CONDITION

In another embodiment of the invention, the measurement of soluble T cell growth factor receptors, T cell surface antigens, or immunologically related molecules can be used to differentially diagnose in a subject a particular physiological condition as distinct from among two or more physiological conditions. To this end, the measured amount of the soluble molecule is compared with the amount of the soluble molecule normally present in a body fluid of a subject with one of the suspected physiological conditions. A measured amount of the soluble molecule similar to the amount normally present in a subject with one of the physiological conditions, and not normally present in a subject with one or more of the other physiological conditions, is indicative of the physiological condition of the subject.

In a specific embodiment of this aspect of the invention, measurement of soluble molecules can be used in the differential diagnosis of renal allograft rejection, especially in distinguishing Cyclosporin A nephrotoxicity. In a particular embodiment of this aspect of the invention, the soluble molecules can be IL2R or related molecules. Similar differential diagnosis of allograft rejection using the methods of the invention can be applied to other organ allografts, including but not limited to liver, heart, and pancreas.

In another specific embodiment measurements of serum CD8 levels may be used in the differential diagnosis of rheumatoid arthritis, as distinguished from other joint diseases.

In yet another specific embodiment of the invention, lymphocytic leukemia may be differentially diagnosed, as distinguished from other leukemia, by measurement and detection of IL2R.

5.4. SOLUBLE T CELL GROWTH FACTOR RECEPTORS, T CELL DIFFERENTIATION ANTIGENS, AND RELATED MOLECULES

Any T cell surface molecule or immunologically related molecule which is present in soluble form in the body fluid at levels which correlate with a disease condition or disorder, or a stage thereof, may be used in the practice of the present invention. T cell surface markers which may potentially be used include but are not limited to those listed in Table I, supra.

Several of the markers listed in Table I, supra, are already known to exist in soluble form. CD2, a receptor for sheep red blood cells, has been detected at higher levels in the sera of certain cancer patients than in normal control patients (Falcao, R. P., et al., 1984, Clin. Lab. Immunol 13: 141-143, Oh, S.-K., et al., 1985, Scand. J. Immunol. 22: 51-60). Leu 2 (OKT8), a surface marker found on suppressor/cytotoxic T cells which may be involved in cellular recognition, has been reported at highly elevated levels in the serum of patients with T cell leukemia (Fujimoto, J., et al., 1983, J. Exp. Med. 159:752-766). Miller et al. (1982, N. Engl. J. Med. 306:517-520) reported the release of Leu 1 into the serum following monoclonal antibody treatment. However, Leu 1 antigen was not detectable in the serum of normal or leukemic patients who had not received antibody therapy.

Other T cell surface molecules whose soluble forms may be measured in accordance with the present invention include but are not limited to T cell growth factor receptors, e.g. interleukin-2 receptor and interleukin-1 receptor In specific embodiments, serum IL2R measurements can be used to predict therapeutic outcomes and monitor the immune status of patients with cancer, immunodeficiencies, autoimmune diseases, or allograft rejection.

5.4.1. ASSAYS FOR MEASUREMENT

Any procedures known in the art for the measurement of soluble molecules can be used in the practice of the instant invention. Such procedures include but are not limited to competitive and non-competitive assay systems using techniques such as radioimmunoassays, ELISA (enzyme linked immunosorbent assay), "sandwich" immunoassays, precipitin reactions, gel diffusion precipitin reactions, immunodiffusion assays, agglutination assays, complementfixation assays, immunoradiometric assays, fluorescent immunoassays, protein A immunoassays, and immunoelectrophoresis assays, to name but a few.

In a preferred embodiment, a sandwich enzyme immunoassay can be used. One description of such an embodiment follows: A monoclonal antibody (capture antibody, mAb 1) directed against the soluble antigen is adsorbed onto a solid substratum. The soluble antigen present in the sample binds to the antibody, and unreacted sample components are removed by washing. An enzyme-conjugated monoclonal antibody (detection antibody, mAb 2) directed against a second epitope of the antigen binds to the antigen captured by mAb 1 and completes the sandwich. After removal of unbound mAb 2 by washing, a substrate solution is added to the wells. A colored product is formed in proportion to the amount of antigen present in the sample. The reaction is terminated by addition of stop solution and absorbance is measured spectrophotometrically. A standard curve is prepared from known concentrations of the soluble antigen, from which unknown sample values can be determined. In particular embodiments, such an assay may be used to determine soluble IL2R levels or soluble T cell antigen levels. In a preferred embodiment for the measurement of IL2R levels, anti-IL2R mAbs 2R12 and 7G7 can be used as the capture and detection antibodies, respectively, in a sandwich immunoassay (such as the CELLFREE TM assay described in Section 15 infra). In a preferred embodiment for the measurement of CD8 antigen levels, anti-CD8 mAbs 4C9 and 5F4 can be used as the capture and detection antibodies, respectively, in a sandwich enzyme immunoassay (such as described in Section 17, infra).

6. SOLUBLE IL2R DETECTION IN PATIENTS

The examples described in Sections 7 through 15 infra demonstrate the detection of soluble or cell free IL2R in patients and the utility of such detection for staging various diseases or conditions. The results indicate that (a) serum IL2R levels are elevated in patients with active lymphatic diseases such as leukemia and lymphoma. In such patients, serum IL2R levels bear a direct relationship with severity of disease and poor prognosis. (b) Serum IL2R levels are generally not elevated in patients with non-lymphatic cancers; however, IL-2 patients receiving IL-2 therapy who are responding to such therapy demonstrate elevated levels of serum IL2R. (c) Serum IL2R levels are elevated in transplant patients who reject allografts; however, serum IL2R levels are not elevated in patients who experience toxicity caused by immunosuppressive drugs used in transplant patients but do not demonstrate true allograft rejection.

The procedures used in these examples are described in the subsections below.

6.1. MONOCLONAL ANTIBODIES

Monoclonal antibodies directed against the IL2R were produced as previously described (Uchiyama, T., et al., 1981, J. Immunol. 126(4):1393-1397; Rubin, L. A., et al., 1985, Hybridoma 4:91-102; Jung, L. K. L., et al., 1984, J. Exp. Med. 160:1957). Additionally, monoclonal antibodies directed against IL2R may be purchased commercially (Becton-Dickenson, California; Coulter Diagnostic, Florida). Although the published monoclonal antibodies (Uchiyama, supra; Rubin, supra; Jung, supra) each recognize IL2R, each of these monoclonal antibodies recognizes a different epitope. Monoclonal antibodies were purified according to established standard methods (Cortheir, G., et al., 1984, J. Immuno. Method 66:75-79). Horseradish peroxidase conjugation was done according to published procedures (Wilson, M. B. and Nakane, P. K., 1978, "Recent Developments in the Periodate Method of Conjugating Horseradish Peroxide (HRPO) to Antibodies", in Immunofluorescence and Related Staining Techniques, Knapp, W., K. Holubar, and G. Wick, eds., Elsevier/North-Holland Biomedical Press, pp. 215-224).

6.2. SOLUBLE IL2R ASSAY

In the examples described in Sections 7 through 14, either the procedure described below or the CELL-FREE ™ Interleukin-2 Receptor Test Kit (T-Cell Sciences, Inc., Cambridge, Mass.) described in Section 15 infra was used to measure the amount of soluble IL2R in clinical samples. In each of these assay procedures, two monoclonal antibodies, each recognizing a different epitope on the target antigen, was used.

6.2.1. PROCEDURE

Soluble IL2R was detected in samples using the procedure outlined below:
(a) Polystyrene microliter wells (Flow Laboratory) were coated overnight at room temperature with 100 ul of an anti-IL2R murine monoclonal antibody (2 ug/ml) in phosphate buffered saline (PBS).
(b) Coating solution was discarded and wells were blocked for 1-2 hours at room temperature with 300 ul of 1% bovine serum albumin (BSA) in Tris-buffered saline containing 25 mM Tris pH 7.4 in 0.05% of Tween 20 and 0.15 M sodium chloride (Tris-Tween buffer).
(c) Wells were washed 3 times with Tris-Tween buffer.
(d) 50 ul sample was added per well, followed by 100 ul diluent containing fetal calf serum (FCS) in Tris-Tween buffer. Wells were incubated 2 hours at 37° C.
(e) Wells were washed 3 times with Tris-Tween buffer.
(f) 100 ul of horseradish peroxidase (Sigma Chemical Co.) conjugated anti-IL2R monoclonal antibody in PBS containing 50% FCS was added per well. Wells were incubated 2 hours at 37° C.
(g) Wells were washed 4 times with Tris-Tween buffer.
(h) 100 ul of 0.2% o-phenylenediamine (OPD) and 0.015% of $H_2O_2$ in 17 mM citric acid, 65 mM dibasic sodium phosphate (citrate-phosphate buffer) was added per well. Plates were incubated for 30 minutes at room temperature.
(i) 50 ul of 2 N $H_2SO_4$ was added to each well and the absorbance of each well was measured at 490 nm in a microtiter plate reader (Dynatech MR600, Dynatech Corp., Alexandria, VA.).

6.2.2. IL2R CONTROL STANDARDS

The results of the immunoassay were expressed in units based on a supernatant standard defined as 1000 units/ml. The supernatant culture fluid was generated according to the following procedure:
(a) Mononuclear white blood cells were isolated from 500 ml of whole blood using the Ficoll-Hypaque procedure as outlined in the manufacturing package insert (Sigma Chemical Co.).
(b) Approximately $1 \times 10^6$ cells/ml of white blood cells were suspended in RPMI-1640 medium containing 10% FCS and 100 units of penicillin-streptomycin (Flow Laboratory).
(c) 2 ug/ml of phytohemagglutinin (PHA - Wellcome Diagnostics) were added to the culture.
(d) After 3-6 days of culture, the supernatant was harvested after removing the cells by centrifugation at $200 \times g$.
(e) Supernatant was saved and assigned a reference value of 1000 units/ml.

6.2.6. FLOW CYTOMETRIC METHOD

Flow cytometric analysis of peripheral blood lymphocytes and tissue culture cells was performed as described previously (Hoffman, R. A., et al., 1980, Proc. Natl. Acad. Sci. U.S.A. 77:4914-4917).

7. THERE IS NO CORRELATION BETWEEN SOLUBLE IL2R LEVEL AND IL2R BEARING LYMPHOCYTES IN VIVO

Figure 1A:
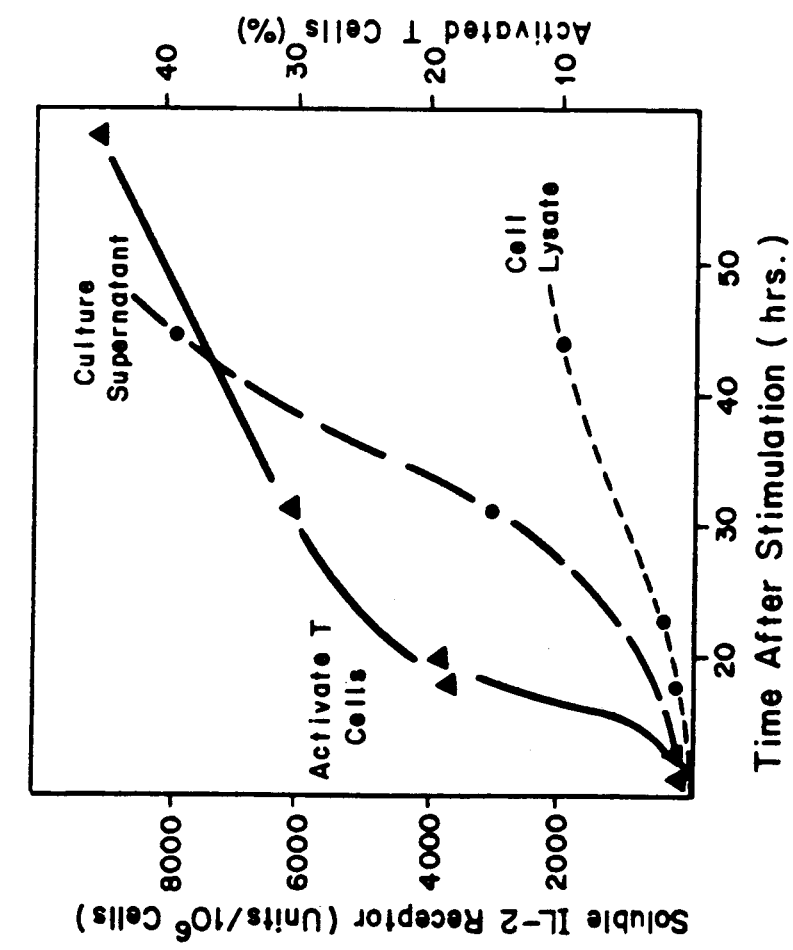
Figure 2:
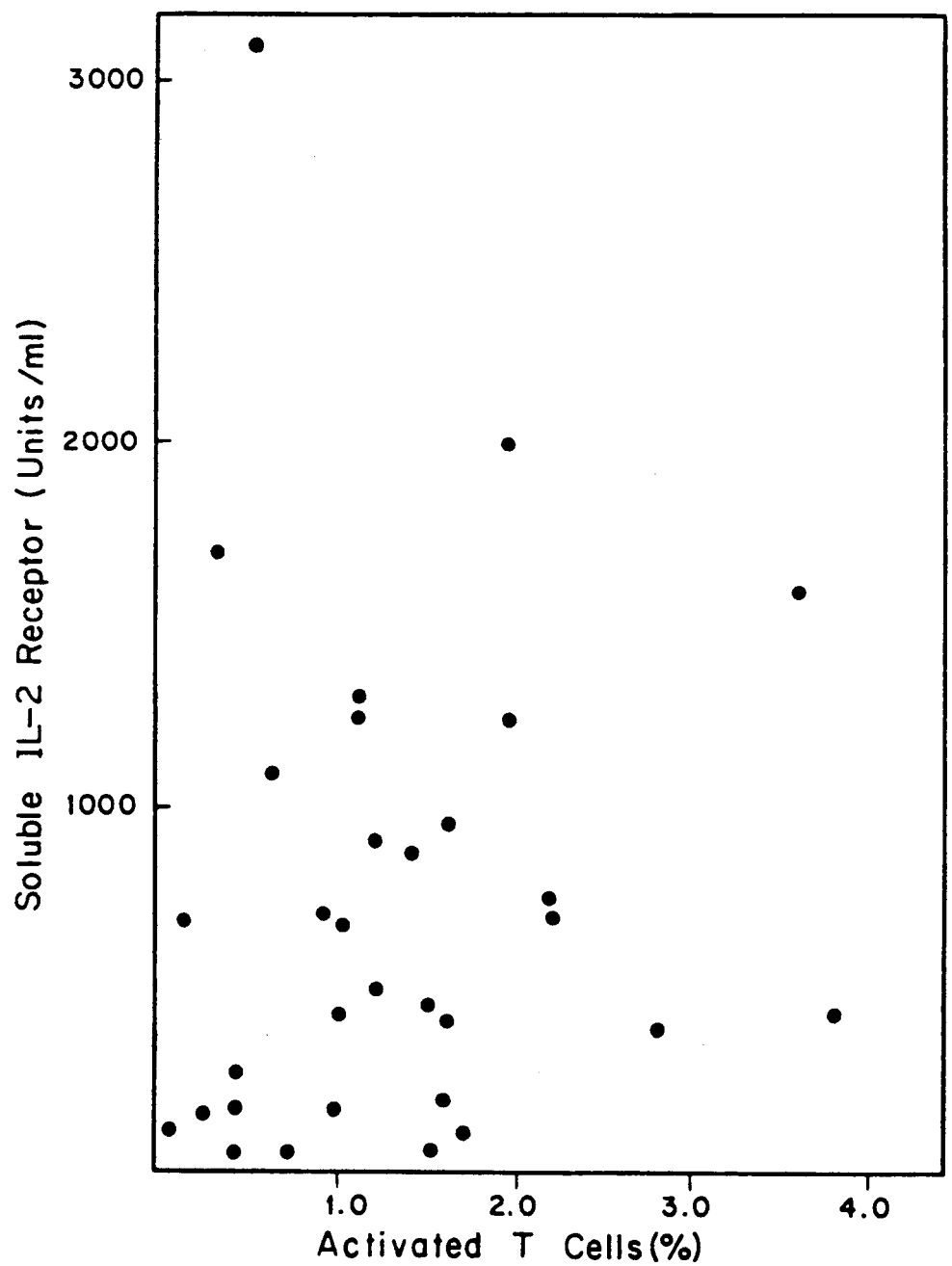

As shown in FIGS. 1A and 1B, the level of serum (soluble) IL2R and the number of T lymphocytes bearing cell surface IL2R is well correlated in a phytohemagglutinin (PHA) stimulated human peripheral blood T cell culture in vitro. However, in vivo, the number of IL2R bearing T cells in circulation correlated poorly with the level of serum IL2R (FIG. 2). Therefore, it is not possible to determine from in vitro experimentation whether serum level of a soluble T cell marker will correlate with an in vivo observation. The clinical use of serum T cell markers can only be determined from direct patient studies.

The level of soluble IL2R has been found to be elevated in a broad spectrum of diseases. The non-specificity of elevated soluble IL2R levels is demonstrated in Table III.

TABLE III

SERUM LEVEL OF SOLUBLE IL-2 RECEPTOR IN PATIENTS

|   | Average Value IL-2 Receptor (units/ml) | Number of Samples Tested |
|---|---|---|
| Healthy Control | 250 | 50+ |
| AIDS Related | 960 | 41 |
| Herpes Virus Infection | 1500+ | 9 |
| Other Infections | 1000 | 5 |
| Systemic Lupus Erythematosis | 620 | 50 |
| Rheumatoid Arthritis | 500 | 20 |

+signifies "greater than".

Specific clinical applications of such measurements are outlined in the examples detailed in the Sections which follow.

8. SERUM MEASUREMENT OF SOLUBLE IL2R MAY BE USED FOR STAGING LEUKEMIA OR MONITORING A THERAPEUTIC TREATMENT

Human T cell leukemia virus (human T lymphotropic virus) Type I (HTLV-I), a sub-group of human T cell leukemia/lymphoma virus, has been closely linked to human adult T cell leukemia (ATL). Identification of HTLV-I as a possible etiological agent of ATL has permitted the development of an assay system for the detection of an antibody directed against the virus in the sera of patients (Saxinger, C. and Gallo, R. C., 1983, Lab. Invest. 49:371-377). Antibody to HTLV-I has been found in virtually all ATL patients. However, HTLV-I seropositive healthy individuals without evidence of ATL are common in ATL epidemic areas of Japan. The differentiation of active leukemia patients from asymptomatic individuals has important diagnostic and prognostic value. Currently no reliable serum test is available for the staging of active versus inactive disease.

Impairment of the host immunosurveillance system is known to influence the development of various cancers in humans and animals. The serum level of IL2R-related macromolecules provides an important distinction of various disease stages in patients. The serum levels of IL2R were measured in patients exhibiting different stages of leukemia using the assay described in Section 6.2. As shown in Table IV below, patients with active T cell malignancy present an elevated level of soluble IL2R as compared to healthy normal and HTLV-I seropositive healthy individuals. Similarly, T cell malignancy patients who are in remission have a decreased level of soluble IL2R.

TABLE IV

SERUM LEVEL OF SOLUBLE IL-2 RECEPTOR IN LEUKEMIA PATIENTS

| Stage of Leukemia | Soluble IL-2 Receptor (units/ml) | Number of Patients |
|---|---|---|
| Active ATL (Japan) | 1765 | 3 |
| Active T Cell Leukemia (U. S.) | 1050 | 7 |
| Seropositive healthy patients | 230 | 17 |
| Leukemia patients in remission | 230 | 4 |

Figure 3:
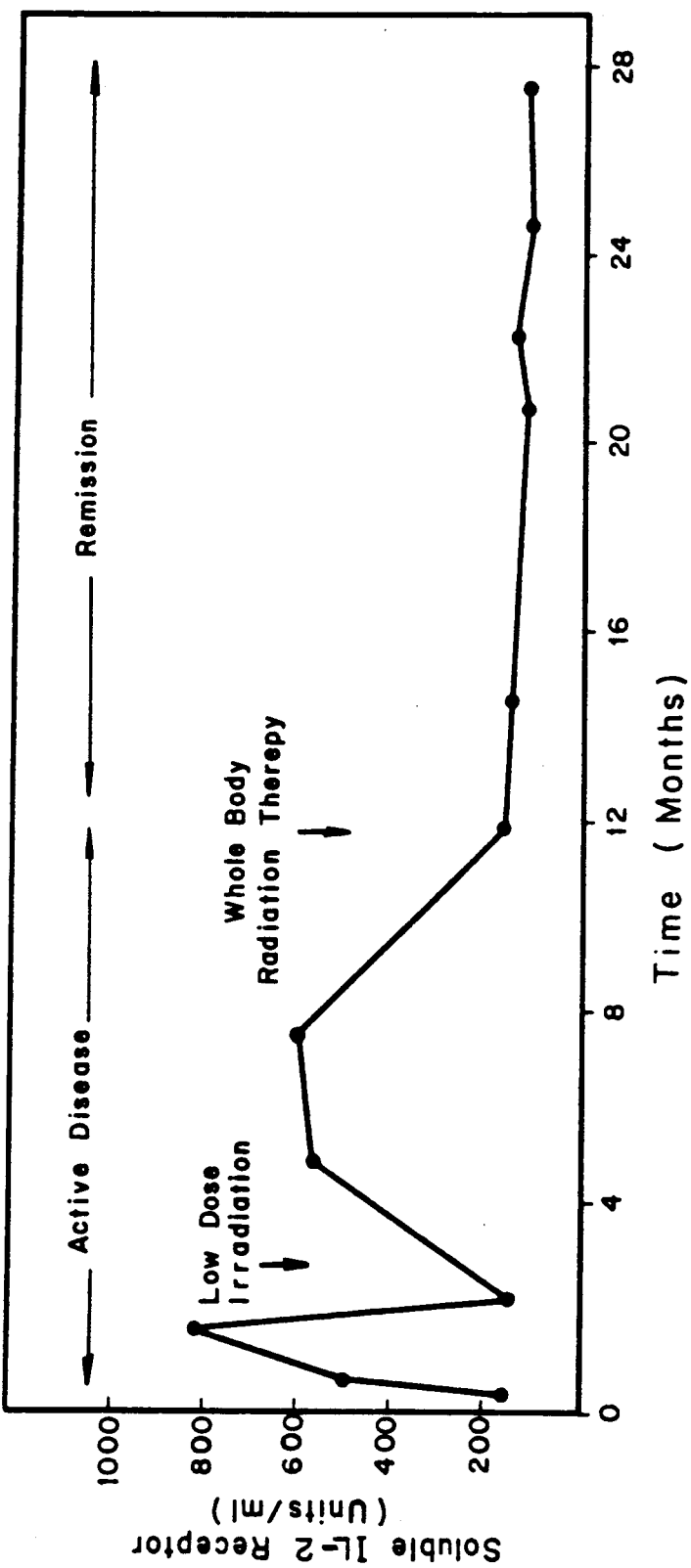

FIG. 3 shows that the amount of IL2R in serum parallels the clinical condition of lymphatic cancer patients. Elevated levels of IL2R in serum indicate failure of therapeutic treatment. After effective treatment, the serum level of IL2R returns to a normal range.

9. HIGH SERUM IL2R LEVELS ARE RELATED TO ADVANCED DISEASE AND A POOR OUTCOME IN CHILDHOOD NON-HODGKIN'S LYMPHOMA

The results presented in the subsection below demonstrate that elevated levels of serum IL2R as measured by the CELLFREE TM assay (Section 15) correlate directly with advanced stages of childhood non-Hodgkins lymphoma and indicate a poor response to the chemotherapeutic regimen selected as well as a poor prognosis.

9.1. PATIENTS AND METHODS

9.1.1. PATIENTS

From 1979 to 1986, 99 consecutive children with non-Hodgkin's lymphoma (NHL) or B-cell acute lymphoblastic leukemia (ALL) were admitted to three clinical trials (Link, M., et al., 1984, Proc. Am. Soc. Clin. Oncol. 3:251; Murphy, S. B., et al., 1986, J. Clin. Oncol. 4:1732-1739; Dahl, G. V., et al., 1985, Blood 66:1110-1114) at St. Jude's Research Hospital, depending on the histologic features and stage of their disease. Serum samples taken before the start of chemotherapy were available for 65 of these patients. The 41 boys and 18 girls with NHL ranged in age from 1.8 to 17.9 years (median, 10.7 years). The 3 boys and 3 girls with B-cell ALL were 2.3 to 10.2 years old (median, 5.8 years). In each case the diagnosis was based on a combination of clinical, anatomic, histologic, cytologic criteria, with addition of immunologic and cytogenetic studies in some instances. The Working Formulation (National Cancer Institute Sponsored Study of Classifications of Non-Hodgkin's Lymphoma: Summary and Description of a Working Formulation for Clinical Usage. The Non-Hodgkin's Lymphoma Pathologic Classification Project, 1982, Cancer 49: 2112-35) was used to classify cases into diffuse small noncleaved-cell, lymphoblastic, or large cell (noncleaved, cleaved and immunoblastic) types. The first category encompasses not only Burkitt's tumor but also lymphomas that have been designated as undifferentiated non-Burkitt's type. The diagnosis of B-cell ALL was made from the presence of surface immunoglobulins on bone marrow blast cells with L3 morphology according to French-American-British (FAB) criteria (Bennett, J. M., et al., 1976, Br. J. Haematol. 33:451-458).

A stage was assigned to each case of NHL with the use of a previously described system (Murphy, S. B., 1980, Semin. Oncol. 7:332-339). Children with localized NHL in favorable sites have stage I or II disease. Stage III includes disseminated disease on both sides of the diaphragm, extensive unresectable intraabdominal disease and all primary epidural or anterior mediastinal tumors without bone marrow or central nervous system (CNS) involvement. Stage IV is defined by initial CNS and (or) bone marrow involvement (less than or equal to 25% blast cells) in addition to other tumor sites. Cases with greater than 25% malignant B cells in the bone marrow were classified as B-cell ALL, representing advanced B-cell NHL in a phase of leukemic evolution. In this study, 30 patients had diffuse small noncleaved-cell NHL (stage I in 8, II in 10, III in 11 and IV in one); 22 had lymphoblastic NHL (stage I in 1, II in 2, III in 14 and IV in 5); 7 had large cell NHL (stage I in 3 and II in 4) and 6 had B-cell ALL.

Soluble IL2R was also measured in 12 children with otitis media who were otherwise normal and ranged in age from 1 to 6 years (median, 3 years).

9.1.2. TREATMENT

Children with stage I or II NHL were treated according to a Pediatric Oncology Group (POG) protocol that employs three cycles of cyclophosphamide, doxorubicin, vincristine and prednisone for remission induction and consolidation therapy and 6 months of 6-mercaptopurine and methotrexate for continuation therapy (Link, M., et al., 1984, Proc. Am. Soc. Clin. Oncol. 3:251). Children with stage III or IV small noncleaved-cell NHL or B-cell ALL received 6 months of intensive treatment with alternating courses of either high-dose fractionated cyclophosphamide followed by vincristine and doxorubicin or coordinated high-dose methotrexate and cytarabine (Murphy, S. B., et al., 1986, J. Clin. Oncol. 4:1732-1739). Patients with stage III or IV lymphoblastic NHL were treated on a protocol designed for high-risk ALL in which teniposide plus cytarabine was added to an otherwise conventional regimen of therapy (Dahl, G. V., et al., 1985, Blood 66: 1110-1114). Informed consent was obtained for all patients, and the investigation was approved by the institution's clinical trials committee.

9.1.3. DETERMINATION OF SOLUBLE IL2R LEVELS

Soluble IL2R was measured using as the CELL-FREE ™ Interleukin-2 Receptor Test Kit (T-cell Science, Inc., Cambridge, Mass.) described in Section 15 infra. Serum levels of IL2R are expressed in units (U)/ml. A reference preparation of 1000 U/ml of supernatant from phytohemagglutinin-stimulated peripheral blood lymphocytes was used as a standard. The normal serum IL2R values in healthy adult donors ranges from 50 to 500 U/ml (mean, 260 U/ml).

9.1.4. DETERMINATION OF SERUM LACTIC DEHYDROGENASE

The total activity of serum lactic dehydrogenase (LDH) was measured with the Monitor Kinetic AMB-610 assay on the KDA analyzer (American Monitor Corp., Indianapolis, Ind.). Samples with enzyme activities greater than 700 U/L were diluted and reassayed; the values obtained were then multiplied by the dilution factor. The normal values for our laboratory range from 30 to 300 U/L.

9.1.5. STATISTICAL ANALYSIS

The Kruskal-Wallis test was used to compare soluble IL2R or serum LDH levels among different subgroups of patients with NHL. The Pearson product-moment correlation (r) and t-test analysis were used to determine the association between soluble IL2R and serum LDH levels. Time-to-failure curves were constructed by the Kaplan-Meier procedure (Kaplan, E. L. and Meier, P., 1958, J. Am. Stat. Assoc. 53:457-481), with differences analyzed by the log rank test (Peto, R. and Peto, J., 1972, J. R. Stat. Soc. 135A:185-216). Time to failure was defined as the interval between achievement of remission and relapse or death due to any cause. Patients who did not enter remission were assigned a failure time of zero. The influence of potentially significant prognostic factors on time to failure was estimated with the Cox proportional-hazards model (Cox, D. R., 1972, J. R. Stat. Soc. B. 34:187-220), which permits comparison of treatment outcome for two or more subsets of patients while simultaneously adjusting for the effect of other factors (covariates) in the model. Final selection of factors for the model depended on whether or not the P value was less than 0.10 after adjustment for other variables already in the model, using a forward stepwise procedure. An IL2R value of 1000 U/ml was chosen as the dividing point between high and low receptor levels because it coincided well with clinically distinct groups of diseases and treatment outcome.

9.2. RESULTS

The most reliable prognostic factors in childhood NHL have been the stage of disease at diagnosis and serum LDH level (Murphy, S. B., et al., 1986, J. Clin. Oncol. 4:1732-1739; Murphy, S. B., 1980, Semin. Oncol. 7:332-339; Arseneau, J. C., et al., 1975, Am. J. Med. 58:314-321; Magrath, I. T., et al., 1984, Blood 63:1102-1111). We report here that high soluble IL2R levels predict a poor treatment outcome even after adjustment for these two factors.

9.2.1. SOLUBLE IL2R LEVELS SHOW A CLEAR RELATIONSHIP TO DISEASE STAGE

Figure 4:
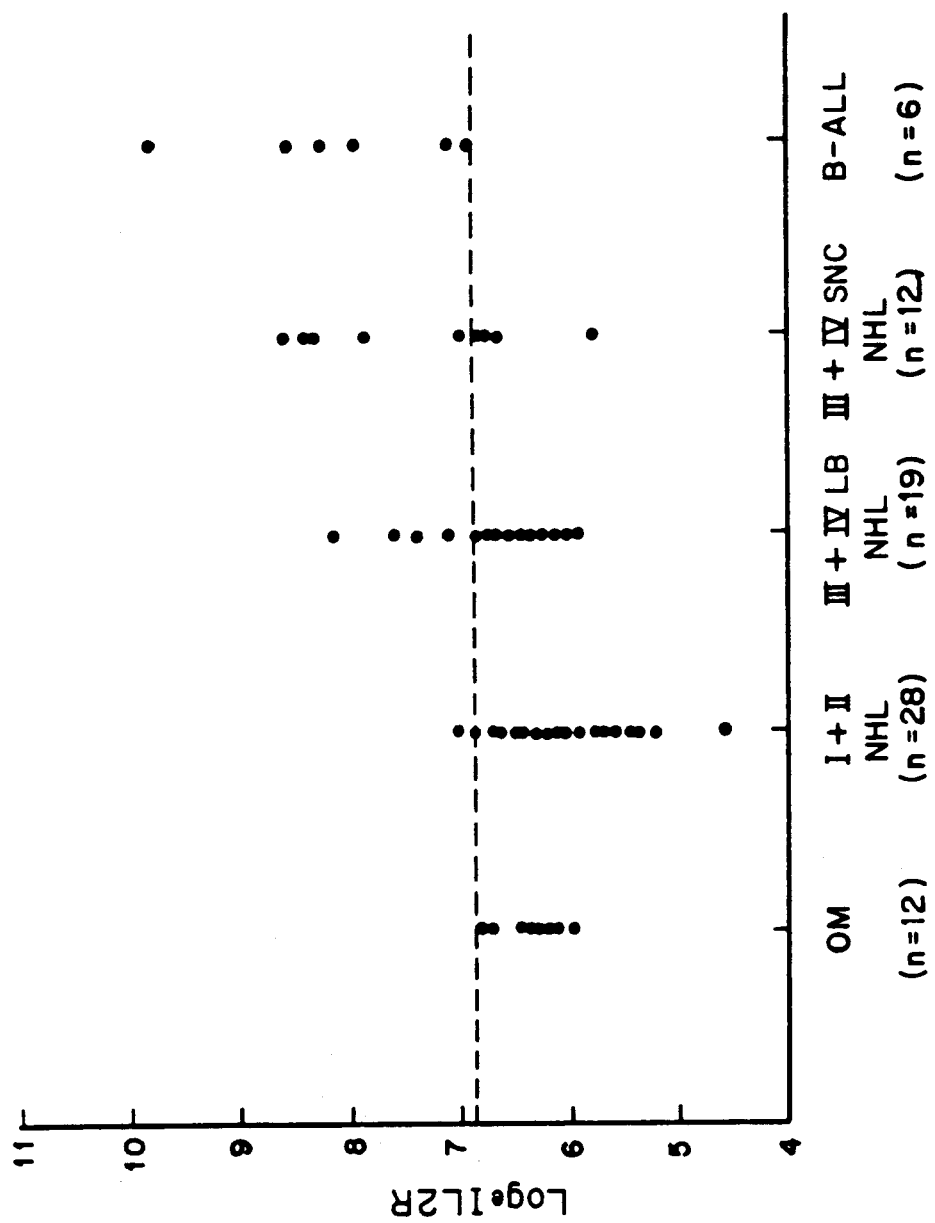

All patients had detectable soluble IL2R levels (FIG. 4), including the 12 children with otitis media (404 to 942 U/ml; median 615 U/ml). The highest values were found in sera from patients with B-cell ALL, 1030-17725 U/ml (median, 3283 U/ml). Children with stage III or IV small noncleaved-cell NHL had soluble IL2R levels of 329 to 5335 U/ml (median, 1832 U/ml), significantly higher than the 376 to 3390 U/ml (median, 808 U/ml) for patients with stage III or IV lymphoblastic NHL (p=0.02). The latter concentrations were in turn greater than those found in stage I or II NHL, 100 to 1143 U/ml (median, 477 U/ml) (p =0.001). Only 1 of the 28 subjects with low-stage disease had a soluble IL2R level above 1000 U/ml.

9.2.2. SOLUBLE IL2R LEVELS SHOW A LINEAR RELATIONSHIP WITH SERUM LDH LEVELS

Figure 5:
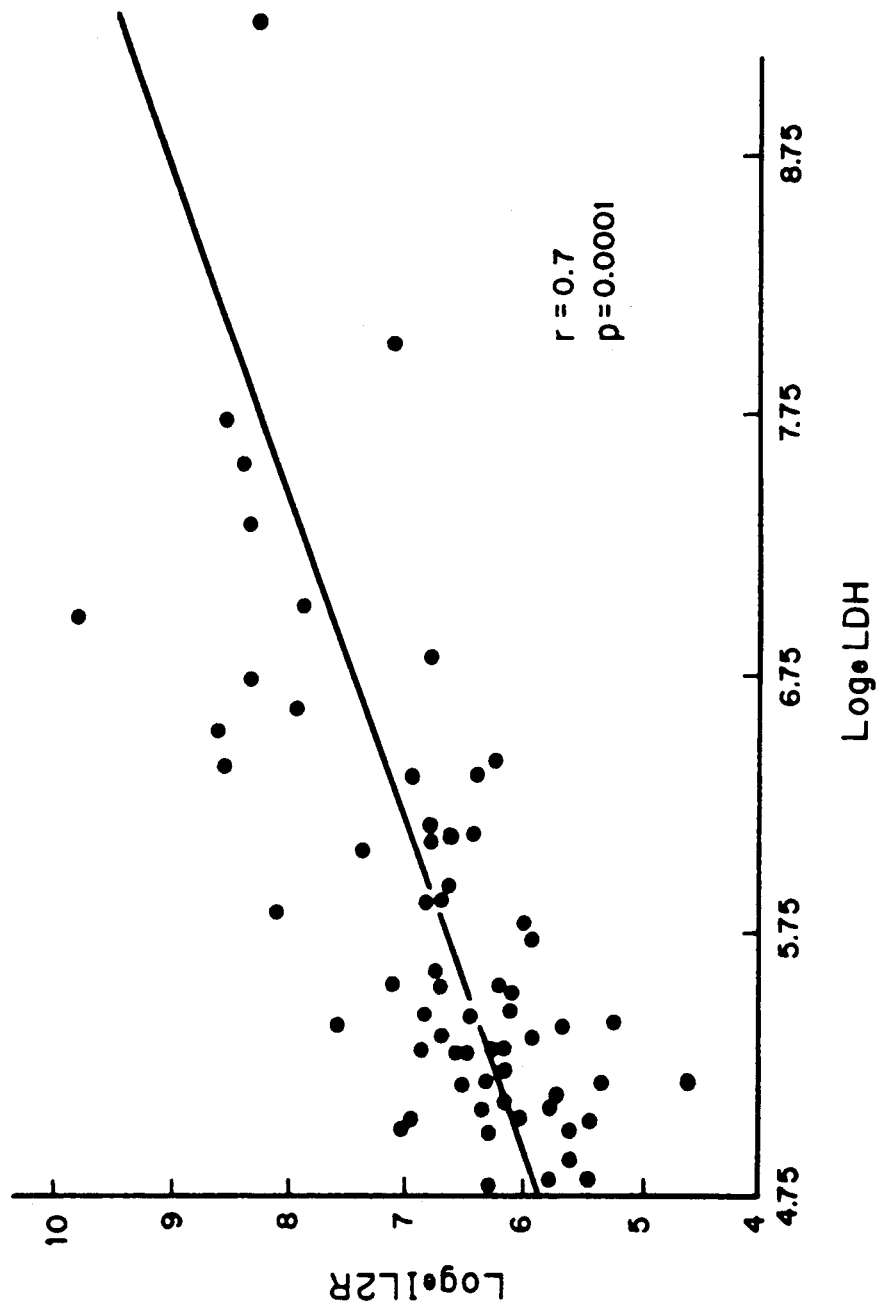

Serum LDH level is a reliable indicator of the total body burden of malignant cells in both ALL (Pui, C.-H., et al., 1985, Blood 66:778-782) and NHL (Murphy, S. B., et al., 1986, J. Clin. Oncol. 4:1732-1739; Arseneau, J. C., et al., 1975, Am. J. Med. 58:314-321; Magrath, I. T., et al., 1984, Blood 63:1102-1111). The distribution of serum LDH levels among the various subgroups of patients showed the same pattern as was noted for IL2R: B-cell ALL is greater than stage III-IV diffuse small noncleaved-cell NHL is greater than stage III-IV lymphoblastic NHL is greater than stage I-II NHL. There was a strong positive correlation between serum IL2R and LDH levels in this study (FIG. 5).

9.2.3. HIGHER SOLUBLE IL2R LEVELS ARE ASSOCIATED WITH A POORER TREATMENT OUTCOME

Figure 6:
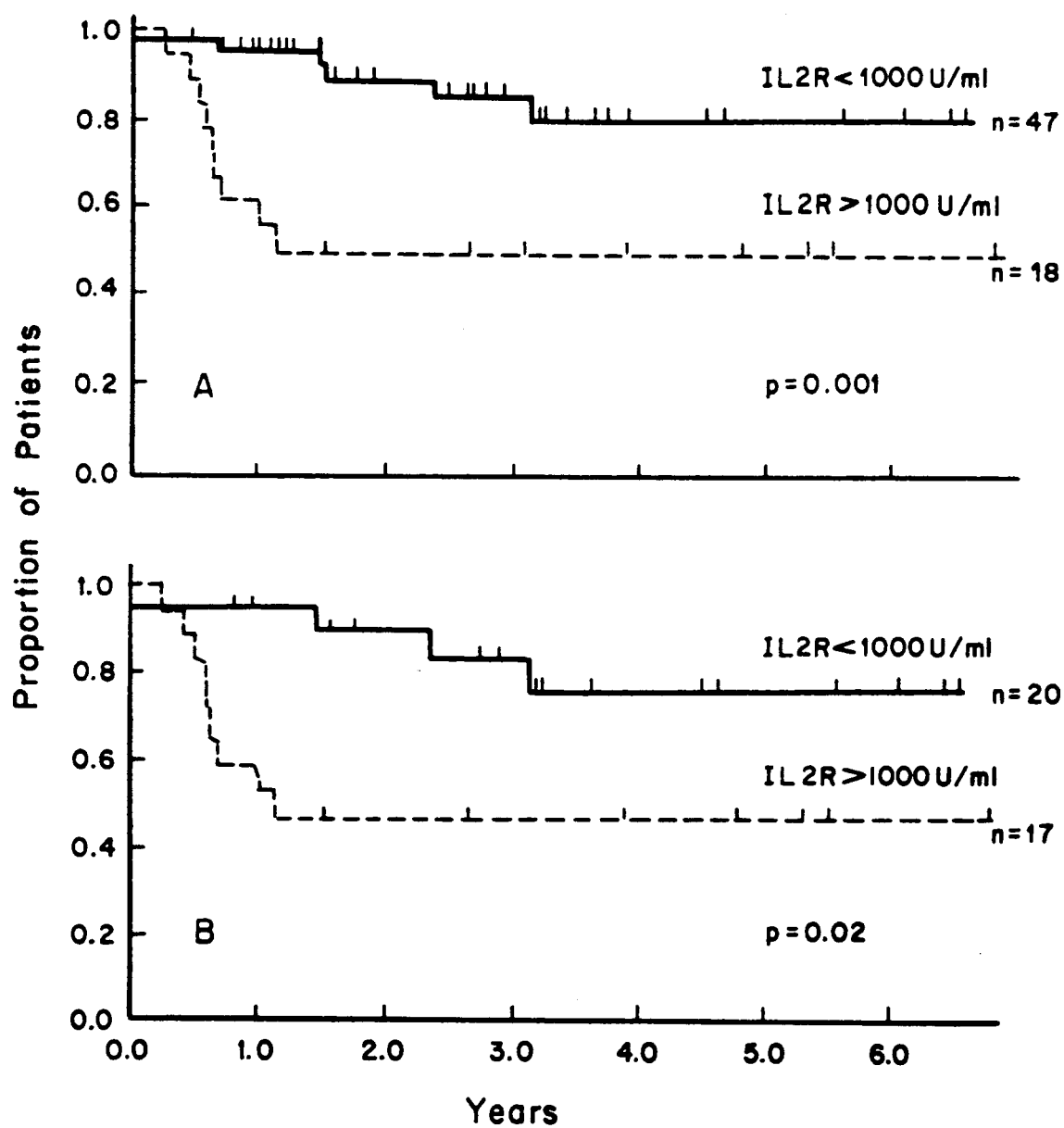

Higher soluble IL2R levels were associated with a poorer treatment outcome. Nine of 18 patients with levels above 1000 U/ml, compared to only 6 of 47 with lower levels, have failed therapy (FIG. 6A, p=0.001). Even when patients with stage I or II disease were excluded, high levels of soluble IL2R were still associated with a poor outcome (FIG. 6B, p=0.02). Because of the possible interrelationships among clinical and biologic risk factors in our patients, a Cox regression analysis was used to assess the relative importance of each factor after adjustment for the effects of other covariates. As shown in Table V, both soluble IL2R level and serum LDH level were found to have independent prognostic value.

TABLE V

RELATIONSHIP OF SERUM IL2R LEVEL AND OTHER PRESENTING FEATURES TO TIME TO FAILURE IN 65 CHILDREN WITH NHL OR B-CELL ALL

| Feature | Category | | P Value[a] |
|---|---|---|---|
| | Better | Worse | |
| Univariate analysis[b] | | | |
| IL2R level (U/ml) | 1000− | 1000+ | 0.004 |
| LDH level (U/L) | 300− | 300+ | 0.007 |
| Stage | I, II | III, IV or B-ALL | 0.017 |
| Histologic type | Lymphoblastic | Diffuse small non-cleaved cell | 0.65 |
| Multivariate model[c] | | | |

TABLE V-continued
RELATIONSHIP OF SERUM IL2R LEVEL AND OTHER PRESENTING FEATURES TO TIME TO FAILURE IN 65 CHILDREN WITH NHL OR B-CELL ALL

| Feature | Category Better | Category Worse | P Value[a] |
|---|---|---|---|
| IL2R level (U/ml) | 1000− | 1000+ | 0.004 |
| LDH level (U/L) | 300− | 300+ | 0.065 |
| Stage | I, II | III, IV or B-ALL | 0.62 |
| Histologic type | Lymphoblastic | Diffuse small non-cleaved cell | 0.48 |

[a] From the likelihood ratio test.
− signifies "less than".
[b] Comparison of time to failure, with use of the Cox proportional-hazards model, between patients with the better-vs.-worse risk feature for relapse in the indicated category, without adjustment for the effects of other variables.
[c] As above, except that stepwise regression analysis was used to identify the best predictors of treatment outcome, taking into account the competing effects of all covariates entered in the Cox model.

The increased serum IL2R levels in our patients could reflect greater release of the receptor from either malignant cells or activated normal lymphocytes. We favor the first explanation because soluble IL2R levels not only correlated with disease stage but also showed a linear relationship with serum LDH levels, a reliable indicator of tumor cell burden.

We conclude that the level of soluble IL2R in children with NHL has independent prognostic significance, higher levels being associated with more advanced disease, greater tumor burden and a poorer outcome.

10. ELEVATED SOLUBLE IL2R LEVEL IN SERUM OF CANCER PATIENTS UNDER THERAPEUTIC TREATMENT WITH IL-2

Generally, patients suffering from non-lymphatic cancers do not exhibit elevated levels of serum IL2R. However, the subsections below demonstrate that such patients receiving IL-2 therapy, who respond favorably to IL-2 therapy, demonstrate elevated levels of serum IL2R.

10.1. SERUM IL2LEVELS IN CANCER PATIENTS TREATED WITH IL-2

Figure 7:
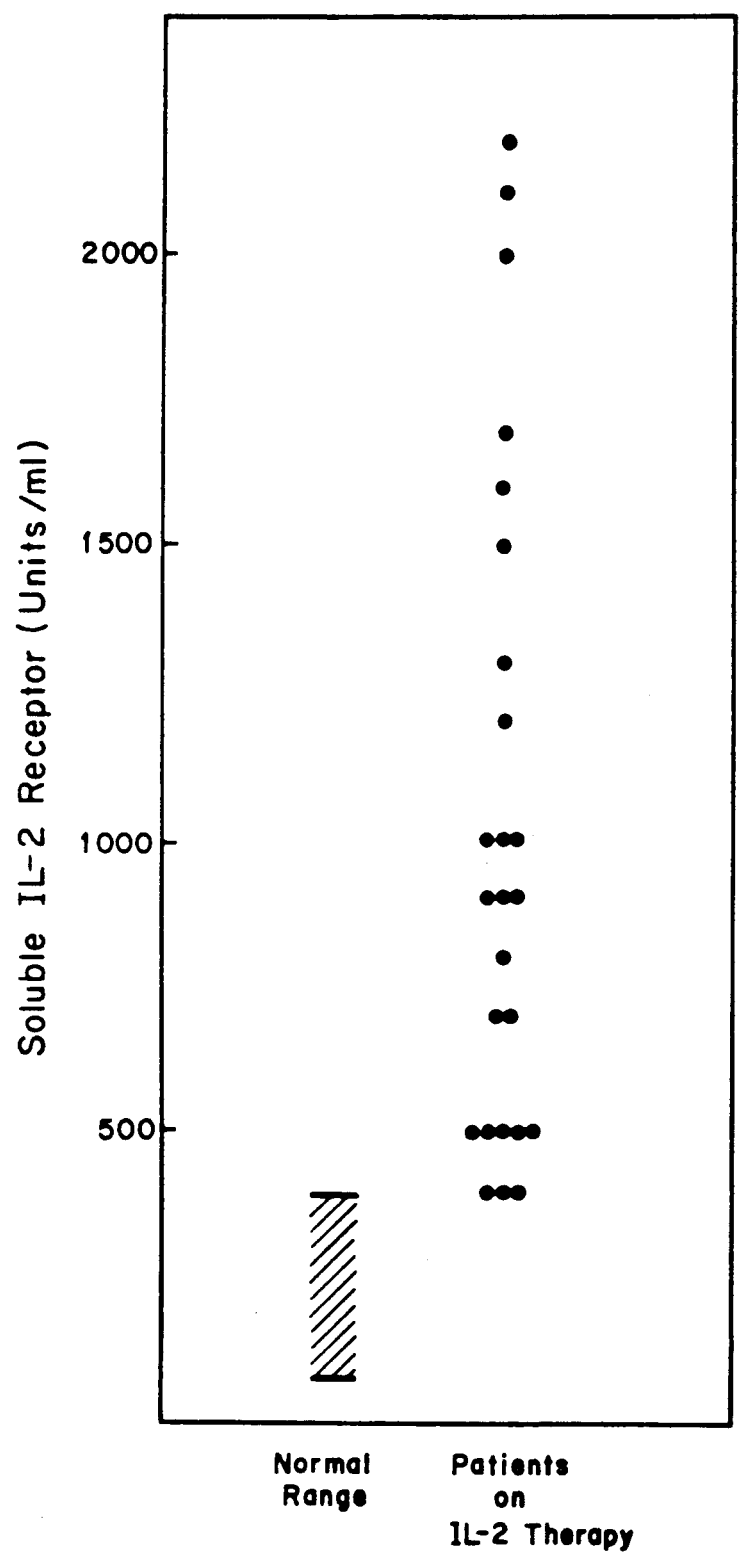

As shown in FIG. 7, the serum level of soluble IL2R is highly elevated in a variety of cancer patients being treated by injection of IL-2. The level of measurable IL2R in serum remains elevated during the therapy treatment. The serum value of IL2R may be used to monitor a patient's response to therapy.

10.2. ELEVATED SERUM IL2R LEVELS IN CANCER PATIENTS RESPONDING TO IL-2 THERAPY

Figure 8:
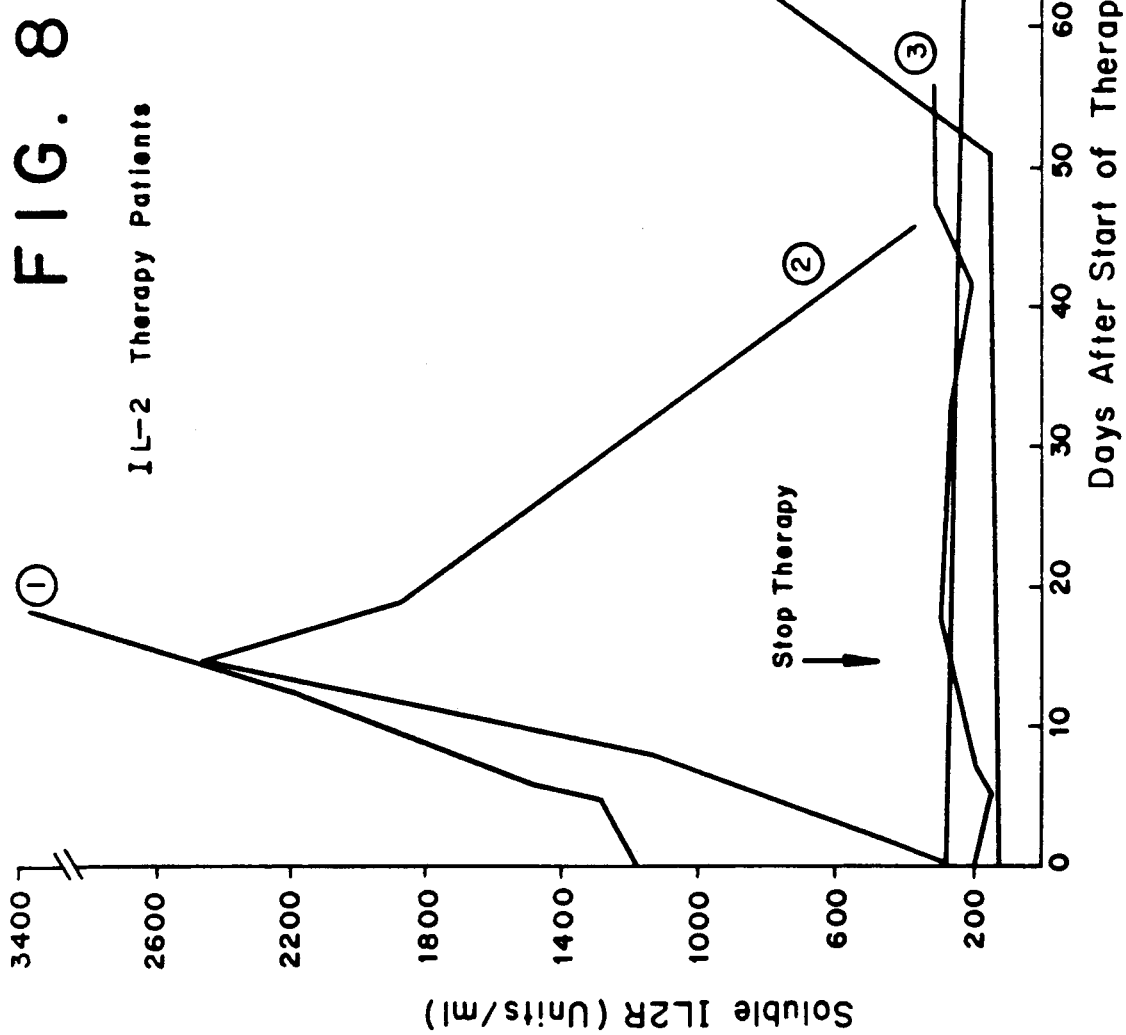

The CELLFREE ™ IL2R assay (Section 15, infra) was used to measure serum IL2R levels in patients with lung carcinoma who were receiving IL-2 therapy. Patients 1 and 2 were infused continuously from day 0 to day 14 with $3 \times 10^6$ U/ml of recombinant IL-2 and showed good response to the therapy. These patients demonstrated elevated levels of serum IL2R (see FIG. 8).

Patients 3, 4 and 5 were infused continuously from day 0 to day 14 with $2 \times 10^6$ U/ml of recombinant IL-2 and showed a poor or no response to the therapy. These patients demonstrated no increase in serum IL2R (see FIG. 8).

11. SERUM LEVEL OF SOLUBLE IL2R MAY BE USED TO DIFFERENTIALLY DIAGNOSE BETWEEN TRANSPLANT REJECTION AND THERAPEUTIC TOXICITY AND TO MONITOR THERAPEUTIC TOXICITY

The immune system plays an important role in tissue transplantation. Graft rejection is primarily a cell-mediated phenomenon, and T lymphocytes are primarily responsible for the rejection of a graft. Therefore, soluble T cell surface macromolecules such as the IL2R may be useful in the monitoring of immune status and graft rejection. The following studies demonstrate this utility. Serum IL2R was measured in patients with renal transplants using the assay described in Section 6.2. Currently, a highly effective approach to prolonging the survival of graft organs is to suppress the cellular immune response using a number of therapeutic reagents, including monoclonal antibodies against human T cells, anti-lymphocyte antiserum, and immunosuppressant drugs. One of the immunosuppressive drugs currently prescribed for many organ transplant recipients is Cyclosporin A (CsA), a fungal-derived cyclic peptide. CsA appears to have specificity for lymphoid cells and inhibits the production of IL-2 in the early time point of T cell activation. However, the clinical use of CsA in transplant patients has serious problems due to the presence of significant toxicity.

Figure 9:
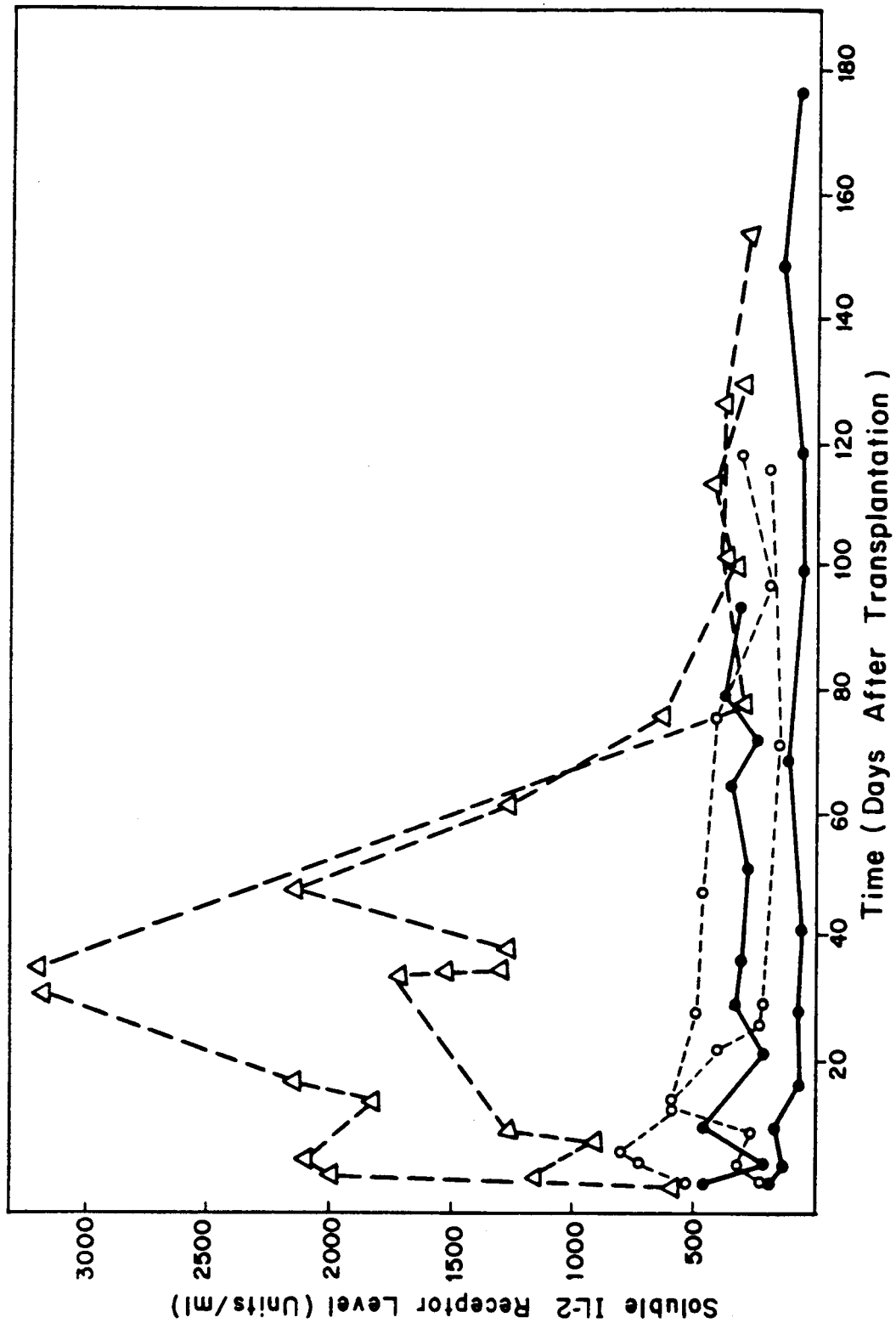

Currently, the most effective diagnostic method of monitoring dysfunction in renal transplantation recipients is to measure serum level of creatinine. However, this monitoring method cannot distinguish between toxicity caused by an immunosuppressant drug such as CsA and true renal rejection (FIG. 9). As shown in Table VI, measurement of IL2R-like macromolecules in patients' serum is useful for distinguishing between CsA toxicity and renal rejection.

TABLE VI
SERUM LEVEL OF SOLUBLE IL-2 RECEPTOR IN RENAL TRANSPLANT PATIENTS MEASURED IN UNITS/ML

| Clinical Samples | Mean | Std. Dev. | No. of Patients |
|---|---|---|---|
| Pre-transplant (dialysis) | 721 | 434 | 18 |
| Normals | 150 | 105 | 20 |
| Stable transplant | 270 | 206 | 89 |
| CsA toxicity | 493 | 241 | 12 |
| Rejection (Before therapy) | 1032 | 584 | 13 |
| Viral infection | 1420 | 555 | 4 |
| During immuno-therapy with antibody OKT3 or ATG | 1758 | 724 | 23 |

In this experiment, serum level of IL2R remained low or slightly elevated in response to CsA toxicity, whereas IL2R level rose in response to renal rejection. Thus, in combination with serum creatinine measurement, the measurement of immune response as indicated by serum level of IL2R is useful to monitor effects of therapeutic treatments. Furthermore, the measurement of IL2R levels is useful as a method of differential diagnosis between CsA toxicity and renal rejection. This noninvasive measurement is preferred over existing methods of differential diagnosis between CsA toxicity and renal rejection which involves the examination of a biopsy specimen from a grafted kidney.

Similar observations have been made in liver transplantation patients. As shown in Table VII, patients with liver transplant rejections have elevated levels of soluble IL2R in their serum. Decreased serum levels of IL2R were found in patients who showed no signs of rejection after transplantation.

TABLE VII

SERUM LEVEL OF SOLUBLE IL-2 RECEPTOR IN LIVER TRANSPLANT PATIENTS MEASURED IN UNITS/ML

| Clinical Samples | Mean | No. Of Patients |
|---|---|---|
| Pre-transplant | 647 | 4 |
| Stable transplant | 600 | 1 |
| Rejection | 1500+ | 3 |

+signifies "greater than".

12. PLASMA IL2R LEVELS IN RENAL ALLOGRAFT RECIPIENTS

In the examples described in the subsections below, the CELLFREE TM Interleukin-2 Receptor Kit was used to measure serum levels of IL2R in renal allograft patients. Those patients who experienced true allograft rejection presented elevated serum levels of soluble IL2R.

12.1. PATIENTS AND METHODS

Thirty-two patients who received an HLA non-identical renal allograft from cadaver or living related donors were studied. Patients were maintained on steroids and cyclosporine (CsA) or azathioprine. Rejection episodes were diagnosed on standard clinical and pathologic grounds (including a progressive elevation of serum creatinine level accompanied by one or more of the following: oliguria, fever, or weight gain). CsA levels were measured in plasma by radioimmunoassay. CsA toxicity was defined as a progressive elevation of serum creatinine level associated with a plasma level of greater than or equal to 700 ng/ml which responded to decreased dosages of CsA. Rejection episodes were treated with pulse steroids, anti-T3 monoclonal antibody (mAb) OKT3 (Ortho Pharmaceuticals) or AT-GAM TM (horse anti-thymocyte globulin, Upjohn).

Plasma (citrate) for IL2R assay was taken before transplantation and at intervals of 1-2 times per week for the first several weeks and at weekly-monthly intervals thereafter, and stored at −70° C. The IL2R assay was done using the CELLFREE TM Interleukin-2 Receptor Test Kit (T Cell Sciences, Inc., Cambridge, Mass.) (see Section 15, infra). The test employs two non-competing monoclonal antibodies to the human IL2R in which the first antibody (mAb 2R12) was coated on the plastic microwells, washed, blocked, and 50 ul of test sample was applied with 100 ul of diluent. After a 2 hour incubation, the wells were washed, and the indicator antibody conjugated to horseradish peroxidase was added. After another 2 hours, the wells were washed, and orthophenylenediamine (OPD) was added. The reaction was quenched after 30 minutes with 1N sulfuric acid and the absorbance was measured at 490 nm. A standard curve was generated using serial dilutions of a supernatant from phytohemagglutinin (PHA) stimulated peripheral blood mononuclear cells which was defined as a value of 1000 units/ml. The summary data (Table VIII) excludes the first 4 patients studied before the values were converted to PHA units. Normal plasma samples were from healthy laboratory personnel.

12.2. PLASMA CONTAINS ELEVATED LEVELS OF SOLUBLE IL2R DURING EPISODES OF RENAL ALLOGRAFT REJECTION

The data for plasma IL2R levels in the tested patients are summarized in Table VIII.

TABLE VIII

| | PLASMA IL2R LEVELS | | |
|---|---|---|---|
| Sample | N | Units/ml[1] | p (t test) |
| Normals | 20 | 150 ± 105 | |
| Pre-Transplant (Dialysis) | 14 | 800 ± 450 | 0.001⁻ vs. Normal |
| Stable Transplant | 63 | 266 ± 205 | 0.02⁻ vs. Normal |
| Rejection | 15 | 1050 ± 637 | 0.001⁻ vs. Stable |
| During OKT3/ATG Therapy | 20 | 1788 ± 726 | 0.004⁻ vs. Rejection |
| Viral Infection | 6 | 1076 ± 654 | 0.001⁻ vs. Stable |
| Cyclosporine Nephrotoxicity | 13 | 430 ± 218 | 0.003⁻ vs. Rejection |

[1]Arbitrary units, based on a PHA supernatant standard defined as 1000 U/ml; data for 28 patients and 20 normal laboratory personnel, mean ± standard deviation.
⁻signifies less "than".

Patients on chronic dialysis (pre-transplant samples) had levels significantly elevated above the normal controls (p less than 0.001). There values fell toward normal levels in the first week after transplantation. Samples from patients with stable renal function showed values slightly above normal (p less than 0.02). In contrast, patients with acute rejection episodes showed levels that averaged significantly higher than stable patients. These samples, taken at a time when the serum creatinine level had risen, but before anti-rejection therapy had begun, had elevated IL2R levels in 10 of 13 rejection episodes. Shortly after treatment with anti-T cell monoclonal antibodies (OKT3 or ATG), IL2R levels increased further. This rise was evident in samples taken as early as one hour after the first dose of mAb OKT3 (mean rise of 36% in 5 paired samples, p less than 0.05). An exception was seen in a patient given mAb ATG prophylactically, who presumably did not have preexisting activated T cells. Patients with CsA nephrotoxicity had levels significantly below those with rejection (p less than 0.003). Three episodes of azotemia (without biopsies) could not be classified (improvement following a reduction of CsA and an increased in other immunosuppression) and were not used for the data analysis Two patients had serious viral infections (cytomegalovirus, herpes simplex virus) and another had a viral syndrome with diarrhea; all showed marked elevation of IL2R levels. A patient with renal failure due to renal artery stenosis (Cr 3-4 mg %) and a patient with hemolytic uremic syndrome (Cr 5-6 mg %) did not show the elevation of IL2R levels seen in the patients with rejection.

In allograft rejection, activated T cells are found in the blood and in the graft (van ES, A., et al., 1984, Transplant. 37:65; Hancock, W. W., et al., 1985, Transplant. 39:430); however, the elevation in the amount of soluble/released IL2R observed in these experiments was unexpected, with the observed level equivalent to that which occurs in vitro in cultures with PHA stimulation. We also found elevated levels of IL2R in certain infections.

Administration of OKT3 or ATG anti-T cell mAbs was followed by a rise in IL2R level, presumably due to release of cellular IL2R consequent to cell injury by the antibodies. An exception to this observation occurred when ATG was given prophylactically. Thus progressive elevation of IL2R levels may be a valuable confirmatory test during anti-T cell antibody therapy.

Patients on chronic dialysis had increased concentrations of IL2R in the plasma. These patients are not known to have increased T cell activation and indeed have been found to have impaired T cell function. The nature of the defect in chronic renal failure remains enigmatic, although evidence points to immunosuppressive factors in uremic serum or plasma (Fehrman et al., 1980 J. Clin. Nephrol. 14: 183). It is possible that the soluble IL2R itself is immunosuppressive, since it is able to bind IL-2 (Rubin, L. A., et al., 1986, J. Immunol. 137:3841-3844) and thus could compete with the IL2R on the T cell surface. The reason for the elevation of IL2R in chronic uremia is not known. The simplest explanation is that the soluble IL2R is normally excreted by the kidney. While further studies are needed to address this question, our initial data argue against a simple relationship between renal function and IL2R levels, since acute azotemia due to certain other causes (renal artery stenosis, hemolytic uremic syndrome, and CsA nephrotoxicity) do not have marked elevations of IL2R as a rule. Whether this relates to the acuteness of the renal failure or other factors e.g., dialysis or immunosuppression) is not known. Nonetheless, the elevated IL2R level in chronic uremia complicates interpretation, particularly in the early postgraft period, before the levels have fallen towards normal.

Our data indicate that the plasma contains increased amounts of immunoreactive IL2R during most episodes of renal allograft rejection, and suggest that assay for plasma/serum IL2R may be useful clinically in the differential diagnosis of renal allograft rejection, especially in distinguishing CsA nephrotoxicity.

13. A COMPARISON OF SERUM IL2R LEVELS AND ENDONYOCARDIAL BIOPSY GRADES IN THE MONITORING OF CARDIAC ALLOGRAFT REJECTION

The current clinical success of cardiac transplantation is related to more effective immunosuppression based on the use of Cyclosporin A and the monitoring of allograft rejection using sequential endomyocardial biopsy (Austen, W. G., and Cosimi, A. B., 1984, N. Engl. J. Med. 311:1436-1438). Endomyocardial biopsy is relatively safe and reliable in adult allograft recipients but it is an invasive technique associated with some morbidity which cannot be performed with ease in infants and small children. Furthermore, the interpretation of biopsies is subjective and it is an expensive monitoring technique. However, endomyocardial biopsy is currently the only accepted means of diagnosing cardiac allograft rejection prior to the onset of potentially irreversible rejection.

Cardiac allograft rejection is primarily a cellular immune reaction involving the activation of T lymphocytes. The process of T cell activation is accompanied by expression of interleukin 2 receptors (IL2R). The experiments described below were designed to test the diagnostic value of serum IL2R levels for monitoring cardiac allograft rejection compared with endomyocardial biopsy. IL2R levels in 56 sera from 6 cardiac transplant patients obtained at the time of endomyocardial biopsy correlated ($r=0.56$) with the histological grade of rejection. For biopsy grades less than 2.0, the mean serum IL2R level was $387\pm41$ units/mL whereas for biopsies diagnosed as rejection (greater than or equal to 2.0), the mean IL2R level was $1017\pm178$ units/mL ($p$ less than 0.0001). The threshold serum level for rejection was calculated to be 545 units/mL. In patient sera with IL2R levels below 545 units/mL, corresponding biopsies showed no evidence of rejection to 40 of 42 samples (specificity $=95\%$). Levels of IL2R above 545 units/mL were present in 8 of 14 instances where the corresponding biopsy showed significant rejection (sensitivity $=57\%$). These data suggest that normal IL2R levels indicate the absence of cardiac allograft rejection whereas elevated IL2R levels are a strong indicator of rejection.

13.1. METHODS

Fifty-six right ventricular endomyocardial biopsies were obtained between 3 and 752 days (mean$\pm$SEM, $159\pm22$) post transplantation from 6 adult orthotopic transplant recipients using standard techniques (Dec. G. W., et al., 1985, N. Engl. J. Med. 312:885-890). At least five fragments of endomyocardium were examined by light microscopy, immunoperoxidase and immunofluorescence for evidence of cardiac allograft rejection. Biopsies were graded prospectively without knowledge of the IL2R levels using a modification of the Stanford criteria (Mason, J. W. and Billingham, M. E., 1980, Progress in Cardiology 9:113-46):

| Grade | Histology |
|---|---|
| 0.0 | Normal |
| 0.5 | Rare foci of perivascular lymphocytic infiltrates |
| 1.0 | Occasional foci of perivascular and/or interstitial lymphocytic infiltrates |
| 1.5. | Multiple foci of perivascular and interstitial lymphocytic infiltrates without myocyte necrosis |
| 2.0 | Multiple foci of lymphocytic infiltrates associated with one or more foci of myocyte necrosis |
| 2.5 | Diffuse interstitial lymphocytic infiltrate containing occasional eosinophils and associated with multiple foci of myocyte necrosis |
| 3.0 | Diffuse lymphocytic infiltrate containing eosinophils and neutrophils, interstitial hemorrhage, edema |

All biopsies were graded with respect to their most severe component. A histological grade of 2.0 or greater was considered indicative of rejection requiring additional Serum obtained with each biopsy for immunofluorescence studies was frozen at $-20°$ C. Aliquots of each sample were analyzed by the double monoclonal antibody sandwich technique using noncompeting monoclonal antibodies to human IL2R (CELLFREE TM, T Cell Sciences, Inc., Cambridge, Mass., see Section 15, infra). The normal IL2R level as determined from 157 blood donor samples was $267\pm119$ ($\pm$SD) units/mL.

All patients were treated with maintenance immunosuppression consisting of prednisone and cyclosporin A. Five patients also received azathioprine. Rejection episodes were initially treated with increased dosages of steroids. Anti-lymphocyte therapy with ATG (antithymocyte globulin) or OKT-3 (Orthoclone OKT3 monoclonal antibody, Ortho Pharmaceutical Corp., Raritan, N.J.) was given to patients with rejection that was unresponsive to additional steroids.

Statistical analyses were performed using RS/1 software (Bolt, Beranek and Newman, Cambridge, Mass.) routines for nonparametric, linear regression and non-linear regression analyses as appropriate. Mean values are expressed with their standard error.

13.2. NORMAL IL2R LEVELS INDICATE THE ABSENCE OF CARDIAC ALLOGRAFT REJECTION WHEREAS ELEVATED IL2R LEVELS STRONGLY INDICATE REJECTION

Figure 10:
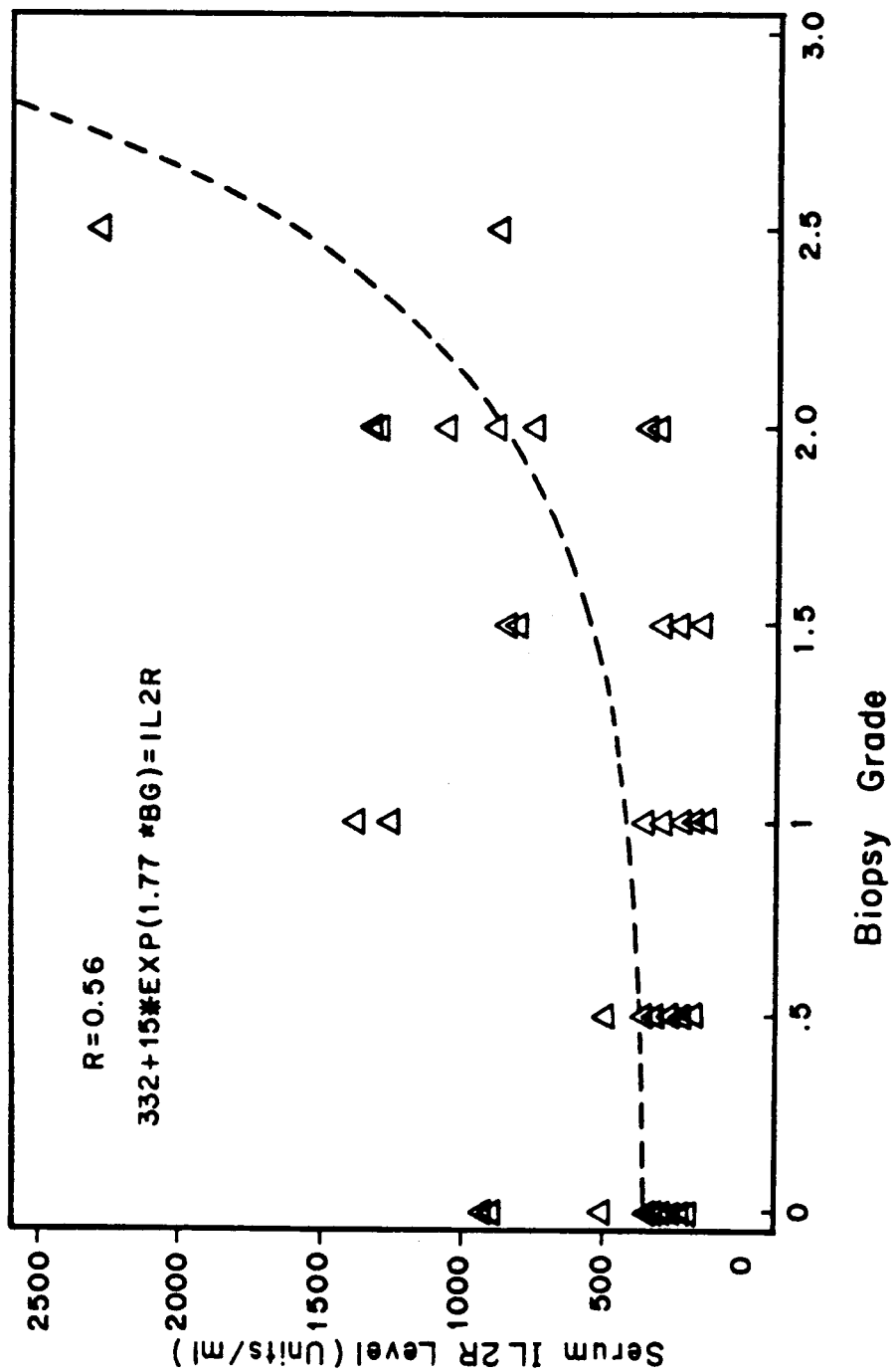
Figure 11:
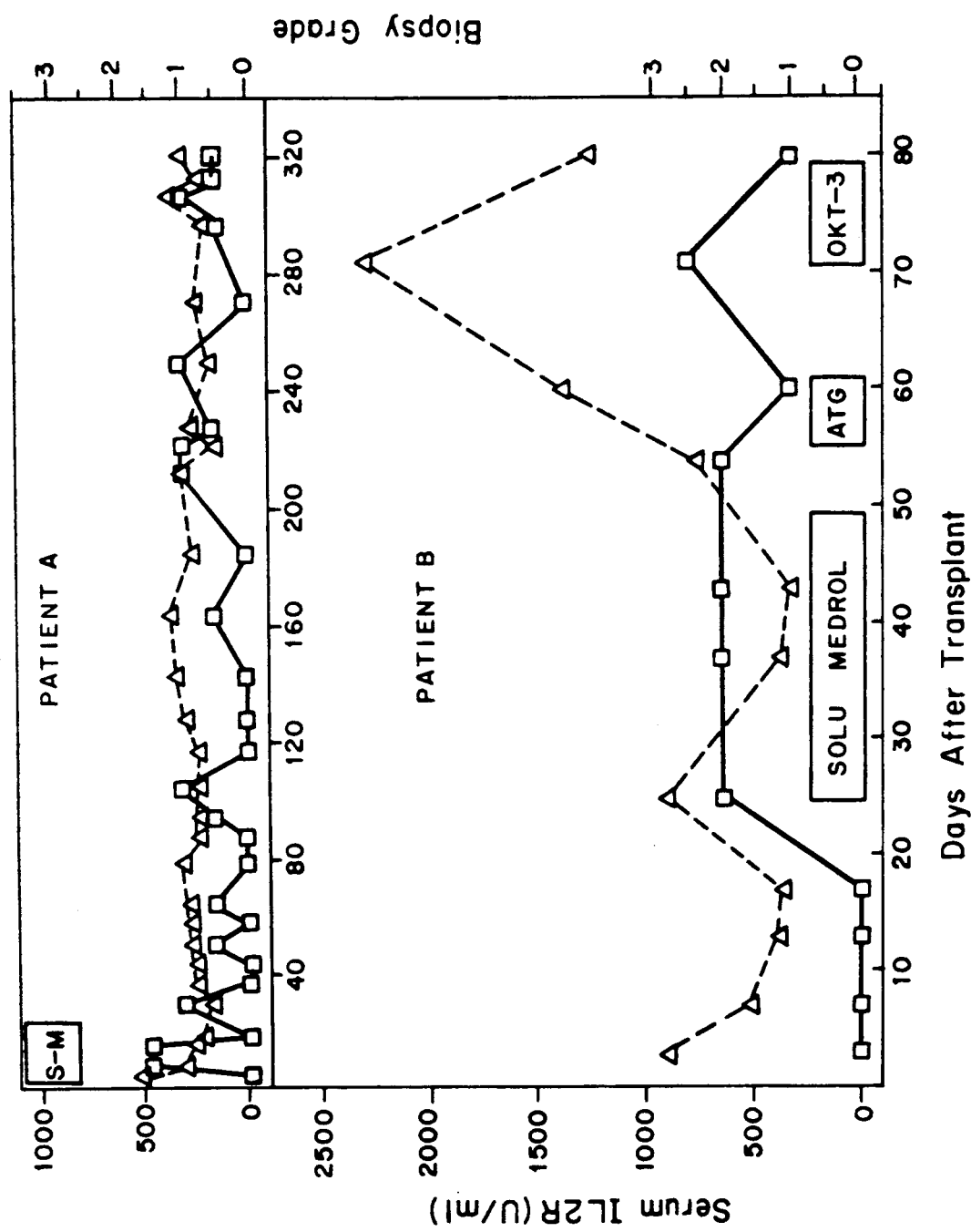

The overall-results are shown graphically in FIG. 10, and complete data for two patients are shown in FIG. 11. For pathological grades of rejection less than 2.0, the mean IL2R level was 387±41 units/mL (n=46, range 156-1386) whereas the mean level for grade 2.0 and higher was 1017±178 units/mL (n =10, range 328-2298). The difference was highly significant with p less than 0.0001. Serum IL2R levels showed an overall linear correlation of 0.56 (p=0.0001) with the histological grade of rejection on corresponding biopsies. However, the data was best fit (r=0.44, f=21, p=0.0001) using the nonlinear regression shown in FIG. 10. The threshold level of IL2R for rejection calculated from this analysis was 545 units/mL.

Levels of IL2R less than 545 units/mL were associated with rejection grades of less than 2.0 in 40 of 42 measurements (specificity =95%). The mean biopsy score for this group was 0.5±0.1 with a range of 0 to 2.0. The two normal IL2R measurements associated with biopsy grades of 2.0 occurred sequentially in Patient B during an episode of rejection under treatment with additional steroids (FIG. 11). Both concomitant biopsies showed resolving rejection, that is, myocyte necrosis was still present but the lymphocytic infiltrate was much less intense than on the initial biopsy diagnosed as grade 2.0 rejection.

Serum IL2R levels greater than 545 units/mL had corresponding biopsy scores of 2.0 or higher in 8 of 14 measurements giving a sensitivity of 57%. The mean biopsy score was 1.6±0.2 with a range from 0 to 2.5. This was significantly different from the mean biopsy score of the normal IL2R group (p =0.0001). In five of six instances where biopsy scores less than 2.0 were associated with serum levels greater than 545 units/mL of IL2R, the elevated level either preceded (n =2; 2d and 11d) or followed an episode of treated rejection (n =3; 9d, 12d and 35d). The sixth instance of elevated level was from the initial post-transplant serum sample of Patient B (FIG. 11) in whom the histological appearance of the corresponding biopsy was grade 0 but the explanted heart showed active lymphocytic myocarditis.

There was no significant correlation between serum IL2R levels and Cyclosporin A levels or the days post transplantation.

The data show that a normal level of circulating IL2R appears to exclude allograft rejection diagnosed on endomyocardial biopsy whereas an elevated serum IL2R level is a strong indicator of cardiac allograft rejection. The apparent low sensitivity (57%) may be more a reflection of the fallibility of endomyocardial biopsy and its interpretation rather than the IL2R measurements in this analysis. Endomyocardial biopsy may miss foci of rejection. In addition, false positives may be due to timing differences in the phenomena being measured, i.e. increases in serum IL2R may occur before actual rejection can be diagnosed by biopsy (as defined by a histological grade of greater than 2.0). In fact, elevated levels of IL2R were associated with rejection in 6 of 6 documented episodes and in two instances, elevated IL2R levels preceded histological evidence of rejection. IL2R levels could possibly prove useful in determining if a treated rejection is ongoing or resolving. Treatment of renal transplant patients with ATG or OKT-3 antibodies results in marked elevations of IL2R. Similarly, following ATG therapy in Patient B, the IL2R level rose dramatically but the corresponding biopsy grade was only 1.0 (FIG. 11). However, Patient B's biopsy eleven days later showed a grade 2.5 rejection and the corresponding IL2R level was 2298 units/mL.

Elevation of IL2R levels also occurs during severe viral infections, certain autoimmune disorders (Nelson, D. L., 1986, Fed. Proc. 45:377 (abstract), T cell leukemias (MacKeen, L., et al., 1986, Fed. Proc. 45:454 (abstract), and chronic renal failure. Patient B, who was transplanted during an episode of recurrent lymphocytic myocarditis, had serum IL2R levels that were elevated immediately post-transplant without evidence of rejection on the biopsy. Thus, the presence of one of the above conditions, and possibly other situations, may result in elevations of IL2R in cardiac transplant patients that are not related to rejection.

The data indicate that serial measurements of IL2R in the serum of cardiac allograft recipients may prove useful in detecting and monitoring rejection. An elevated serum IL2R level, even in the presence of other diseases that elevate IL2R, indicates the need for endomyocardial biopsy to confirm or exclude rejection. The finding of normal serum IL2R levels appears to exclude rejection and thus may be used to forestall performance of endomyocardial biopsy. Measurement of IL2R levels may prove especially useful in infants and small children with cardiac allografts in whom the endomyocardial biopsy is associated with higher risks and more technical difficulty. This approach may prove valuable in reducing both the morbidity and the expense of managing the cardiac allograft patient.

14. SERUM MEASUREMENT OF SOLUBLE IL2R MAY BE USED FOR STAGING VIRAL INFECTIONS

Acquired Immune Deficiency Syndrome (AIDS) is characterized by a severe deficiency of cellular immunity, increased opportunistic infections, and certain malignancies. The human T cell leukemia (T-lymphotropic) virus Type III (HTLV-III) has been closely linked with the disease, and patients with the active disease exhibit severe T cell defects. Clinically, AIDS is manifested by profound lymphopenia and marked reduction of T cell function. However, patients infected with HTLV-III virus (HTLV-III seropositive) do not necessarily exhibit any clinical abnormality. It is therefore essential to distinguish various clinical subgroups of patients who have been exposed to HTLV-III virus and those who have AIDS-related illnesses, e.g. AIDS related complex (ARC).

Figure 12:
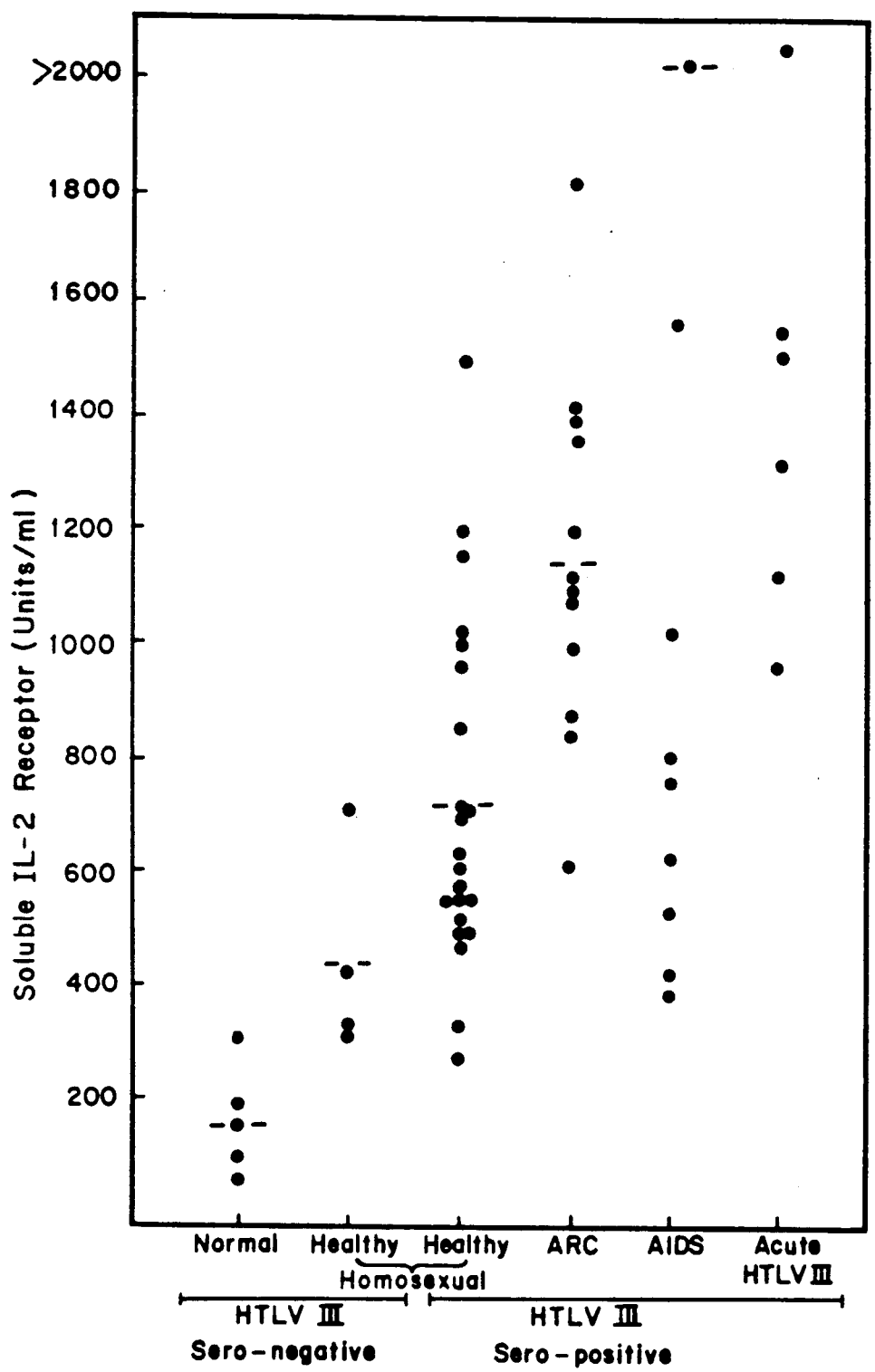

As shown in FIG. 12, the level of serum IL2R correlated with activities of the disease. Therefore, the measured value of soluble IL2R in serum, in conjunction with other clinical tests, provides an index of the severity of the disease in the subject.

15. CELLFREE ™ ENZYME IMMUNOASSAY FOR THE DETECTION OF SOLUBLE, RELEASED IL2R

The subsections below describe a serum immunoassay test kit, using two distinct murine monoclonal antibodies directed against different epitopes of the IL2R for the detection of a cell-free T cell IL2R in serum or plasma. The CELLFREE ™ Interleukin-2 Receptor Test Kit (T Cell Sciences, Inc., Cambridge, Mass.) is a direct enzyme immunoassay for the quantitative detection of released, soluble IL2R in human serum (see also, Rubin et al., 1985, J. Immunol. 135:3172–3177). Accurate quantitation of the serum level of IL2R may be important in characterizing immune disorders, in monitoring disease activity, and in evaluating the efficacy of immunotherapeutic treatment of such disorders.

The CELLFREE ™ Interleukin-2 Receptor Test was used to detect cell free IL2R in various patient and control sera. The soluble or released form of IL2R was found to be elevated in the serum of patients with leukemia and certain immunological disorders. The level of serum IL2R in active adult T cell leukemia (ATL) patients was highly elevated, but remained low in HTLV-1 seropositive asymptomatic patient group.

15.1. PRINCIPLES OF THE METHOD

The CELLFREE ™ Interleukin-2 Receptor Test Kit is a sandwich enzyme immunoassay for the determination of IL2R levels in human serum or plasma. An anti-IL2R monoclonal coating antibody is first adsorbed onto polystyrene microtiter wells. IL2R present in the sample or standard binds to the antibody coated well; unreacted sample components are removed by washing. An enzyme conjugated anti-IL2R monoclonal antibody directed against a second epitope on the IL2R molecule binds to the IL2R captured by the first antibody and completes the sandwich. After removal of unbound enzyme-conjugated anti-IL2R by washing, a substrate solution is added to the wells. A colored product is formed in proportion to the amount of IL2R present in the sample. The reaction is terminated by addition of stop solution and absorbance at 490 nm is measured. A standard curve is prepared from four IL2R standards. Unknown values are determined from the standard curve.

15.2. CELLFREE ™ Test Kit Components and Suggestions

Each CELLFREE ™ Interleukin-2 Receptor Test Kit has reagents sufficient for 96 wells. The expiration date for the complete kit is stated on the outer box label and the recommended storage temperature is 2°–8° C.

15.2.1. REAGENTS SUPPLIED (a) Anti-IL2R Coating Antibody—1 Vial
   Each vial contains murine monoclonal antibody to human interleukin-2 receptor. Store at 2°–8° C.
(b) HRP Conjugated Anti-IL2R Antibody —1 Vial
   Each vial contains horseradish peroxidase (HRP) conjugated murine monoclonal antibody to human interleukin-2 receptor. Store at 2°–8° C.
(c) Sample Diluent—1 vial
   Each vial contains serum protein in a buffered solution. Store at 2°–8° C.
(d) Interleukin-2 Receptor (IL2R) Standards—4 vitals
   Each vial contains released or soluble human interleukin-2 receptor (IL2R) in a buffered solution. Store at 2°–8° C.
(e) OPD Tablets—1 vial
   Each vial contains 14 OPD tablets composed of o-phenylenediamine in an inert binder. Store dessicated at 2°–8° C.
Also supplied:
(f) 96 Well Microtiter Plate with Holder
   Each plate consists of twelve 8-well strips with holder. Store uncoated plates at 2°–26° C.
(g) Directions for Use.

15.2.2. MATERIALS REQUIRED BUT NOT PROVIDED

Reagents

The following reagents must be prepared according to directions in Section 15.2.5, infra. Following the name of each reagent is a list of components needed to prepare that reagent. Each reagent should be made with distilled, deionized water.
(a) PBS Coating Buffer: A commercially available isotonic phosphate buffered saline (PBS) (Dulbecco's PBS without calcium or magnesium is recommended) or NaCl, KCl, $KH_2PO_4$, $Na_2HPO_4.7H_2O$; thimerosal.
(b) Washing Buffer: PBS Coating Buffer (Reagent a.) plus polyoxyethylenesorbitan monolaurate (Tween 20).
(c) Blocking Buffer: Washing Buffer (Reagent b.) plus bovine serum albumin (a neutral pH, fatty acid free preparation is recommended).
(d) Substrate Buffer: Citric acid monohydrate, $Na_2HPO_4.7H_2O$, thimerosal, 30% hydrogen peroxide.
(e) Stop Solution: Concentrated $H_2SO_4$.

Material

Precision pipettes with disposable tips:
   50 and 100 ul micropipettes
   50–200 ul adjustable multiwell pipettor.
Disposable reagent troughs for multiwell pipettor.
Beakers, flasks, cylinders necessary for preparation of reagents.
Microtiter plate washing/aspiration device.
Constant temperature air incubator, 37°±2° C.
Disposable pipettes and test tubes for preparation of OPD (o-phenylenediamine) Substrate Solution.
Microtiter plate reader for measurement of absorbance at 490 nm.

15.2.3. REAGENT PRECAUTIONS

The following precautions are suggested:
Do not mix reagents from different kit lots.
Do not use reagents beyond expiration date on label.
In order to avoid reagent contamination, use disposable pipette tips and/or pipettes.
Sodium azide inactivates HRP. Solutions containing sodium azide should not be used in this assay.
Do not expose OPD reagents to strong light during storage or incubation.
Avoid contact of OPD and Stop Solution with skin and mucous membranes.
If these reagents come into contact with skin, wash thoroughly with water.
Avoid contact of OPD Tablets, OPD Substrate Solution and Stop Solution with any metal surfaces.
Disposable glassware or test tubes are recommended for OPD substrate Solution. If nondisposable glassware is used, it should be acid washed and thoroughly rinsed with distilled, deionized water.

15.2.4. SPECIMEN COLLECTION AND HANDLING

A venous blood sample is collected aseptically. Serum or EDTA plasma is suitable for use in the assay. Remove the serum or plasma from the clot or red cells, respectively, as soon as possible after clotting and separation.

Samples containing a visible precipitate should be clarified prior to use in the assay. Grossly hemolyzed or lipemic specimens should not be used.

Samples can be stored up to seven days at 2°–8° C. If the length of time between sample collection and analysis is greater than seven days, it is preferable to store the sample frozen. Freeze-thaw cycles should be avoided since they may denature the interleukin-2 receptor molecule.

Prior to assay, frozen sera or plasma should be brought to room temperature slowly and gently mixed by hand. Thawing samples in a 37° C. bath, vortexing, or sharp agitation of samples should be avoided.

Sodium azide inactivates HRP. Therefore, specimens containing sodium azide should not be used in this assay.

15.2.5. REAGENT PREPARATION

Except for the OPD Substrate Solution, the following reagents should be prepared prior to Plate Coating, Section 15.2.6., infra:

PBS Coating Buffer

A commercially available isotonic phosphate buffered saline (Dulbecco's PBS, without calcium or magnesium) is recommended. Alternatively, the laboratory may prepare its own PBS using the following procedure:

Dissolve:
8.00 g NaCl
0.20 g $KH_2PO_4$
0.20 g KCl
2.16 g $Na_2HPO_4.7H_2O$
in approximately 800 ml of distilled, deionized water. Add distilled, deionized water to a final volume of 1.00 liter. Verify that the buffer is at pH 7.4±0.2. Mix well.

For either commercially available or laboratory prepared PBS, 0.10 g thimerosal is added as a preservative. Mix well. Store at 2°–26° C. for up to 6 months.

Washing Buffer

Add 0.40 ml of polyoxyethylenesorbitan monolaurate (Tween 20) to 800 ml of PBS Coating Buffer. Mix well. Store at 24°±2° C. for up to 30 days. The Washing Buffer is stable for 30 days. Washing Buffer may be prepared as needed according to Table IX:

TABLE IX

| Procedure | PBS Coating Buffer (ml) | Tween 20 (ml) |
| --- | --- | --- |
| Assaying 0–32 Tests | 400 | 0.2 |
| Assaying 33–64 Tests | 600 | 0.3 |
| Assaying 65–96 Tests | 800 | 0.4 |

Blocking Buffer

Add 1.0 g bovine serum albumin to 100 ml of Washing Buffer. Mix well. Store at 2°–8° C. for up to 30 days before use.

Substrate Buffer

Dissolve:
0.36 g citric acid-monohydrate
1.74 g $Na_2HPO_4.7H_2O$
0 01 g thimerosal
in approximately 80 ml of distilled, deionized water. Add distilled, deionized water to a final volume of 100 ml. Mix well. Verify that the buffer is at pH 6.3±0.2.

Add 75 ul of 30% $H_2O_2$. Mix well. Store at 2°–8° C. for up to 60 days.

Stop Solution (2N $H_2SO_4$)

Add 5.8 ml concentrated $H_2SO_4$ carefully to approximately 80 ml of distilled, deionized water (acid must be added to water). Add distilled, deionized water to a final volume of 100 ml. Mix well. Store at 2°–26° C. for up to 6 months.

The following reagent should be prepared approximately 30 minutes prior to the end of the incubation with conjugate (Section 15.2.7., infra).

OPD Substrate Solution (a) For each strip of 8 wells used, pipette 1.0 ml of Substrate Buffer into a clean glass test tube; (b) Add one OPD Tablet for each ml of Substrate Buffer in the test tube. OPD Tablets should be transferred using nonmetallic forceps or equivalent. Cover the test tube securely and vortex frequently until all OPD Tablets have dissolved. Use within 30 minutes.

15.2.6. SUGGESTED PLATE COATING PROTOCOL

The following protocol is recommended (N.B. the entire 96 well microtiter plate should be coated at the same time):

(a) Measure 11.9 ml of PBS Coating Buffer into a clean test tube or flask. Add 0.1 ml of Anti-IL2R Coating Antibody. Mix well.
(b) Dispense 100 ul of this solution into each well for the entire microtiter plate.
(c) Cover the plate with a plastic sealer and incubate at room temperature (24°±2° C.) in a humid environment for 16–72 hours.
(d) Discard coating solution from all wells.
(e) Add 300 ul of Blocking Buffer to each well for the entire microtiter plate.
(f) Replace the plastic sealer and incubate the plate for 2 hours at 37°±2° C.
(g) If samples are to be run immediately, proceed with assay protocol. If samples are to be run at a later time, store antibody coated wells containing Blocking Buffer covered at 2°–8° C. until use. Wells are stable for up to 45 days after coating.

15.2.7. SUGGESTED ASSAY PROTOCOL

This assay can be performed only after Plate coating, Section 15.2.6., supra, has been completed:

(a) Mix all reagents thoroughly without foaming before use.
(b) Determine the number of strips required to test the desired number of patient samples plus 10 wells needed for running blanks and standards (8 wells per strip). Remove unneeded strips From holder and store at 2°–8° C., covered with a plastic sealer.
(c) Discard Blocking Buffer from coated wells.
(d) Wash the wells 3 times with Washing Buffer. Discard Washing Buffer after each wash.
(e) Remove residual Washing Buffer by tapping the inverted plate on clean absorbant paper.
(f) Leaving the blank wells empty, pipette 50 ul of standard or sample, in duplicate, into antibody coated wells.
(g) Leaving the blank wells empty, add 100 ul of Sample Diluent to all other wells. Care should be taken to avoid cross contamination of samples.

(h) Cover the wells with a plastic sealer and incubate at 37°±2° C. for 2 hours in a constant temperature air incubator.

(i) Remove and discard sealer. Aspirate solution from all wells. Wash wells 3 times with approximately 350 ul of Washing Buffer, with thorough aspiration between washes.

(j) Leaving the blank wells empty, add 100 ul of HRP-Conjugated Anti-IL2R Antibody to all other wells.

(k) Cover with a fresh plate sealer and incubate at 37°±2° C. for 2 hours in a constant temperature air incubator. Approximately 30 minutes prior to the end of incubation with conjugate, prepare OPD substrate solution as directed in section 15.2.5. supra.

(l) Remove and discard sealer. Aspirate solution from all wells. Wash wells 3 times with approximately 350 ul of Washing Buffer with thorough aspiration between washes.

(m) Pipette 100 ul of OPD Substrate Solution into all wells, including blank wells. Incubate uncovered for 30 minutes at room temperature (24°±2° C.).

(n) Pipette 50 ul Stop Solution into all wells, including blank wells.

(o) Read absorbance of wells at 490 nm versus substrate blank. The absorbance should be read as soon as possible after the completion of the assay, but may be read up to 2 hours after addition of Stop Solution when wells are kept protected from light at room temperature. See Section 15.2.10, infra.

15.2.8. CONSTRUCTION OF A STANDARD CURVE (a) Record the absorbance at 490 nm for each standard well.

(b) Average the duplicate values and record the averages.

(c) Plot the absorbance (vertical axis) versus the IL2R concentration in U/ml (horizontal axis) for the standards using a linear scale.

(d) Draw the best fitting curve.

15.29. PATIENT SAMPLES (a) Record the absorbance at 490 nm for each patient sample well.

(b) Average the duplicate values and record the averages.

(c) Locate the average absorbance value which corresponds to each sample on the vertical axis and follow a horizontal line intersetting the standard curve. At the point of intersection, read the IL2R concentration (U/ml) from the horizontal axis.

15.2.10. LIMITATIONS

Since assay conditions may vary from assay to assay, a standard curve should be established for every run. Since cross contamination between reagents will invalidate the test, disposable pipette tips should be used. Reusable glassware should be washed and thoroughly rinsed of all detergent before use. Disposable flasks or glassware are preferred. Thorough washing of the wells between incubations is required:

(a) Completely aspirate well contents before dispensing fresh wash solution.

(b) Fill with wash solution to the top of the well for each wash cycle (approximately 350 ul).

(c) Do not allow wells to sit for extended periods between incubation steps.

Only samples with absorbance values falling within the range of the standard curve should be assigned an IL2R concentration from the curve. Samples with absorbance above the highest standard can be diluted with sample diluent and retested. Recommended dilution is 1/10 (50 ul sample plus 450 ul sample diluent). A small percentage of samples may need greater dilution. The correct concentration of IL2R is then obtained by multiplying the IL2R level in U/ml of the diluted sample (from the standard curve) by the dilution used for testing.

Using the CELLFREE TM Interleukin-2 Receptor Test Kit, soluble or released IL2R values were not affected by the addition of up to 2 ug/ml of recombinant IL-2 to test samples.

15.3. CELLFREE TM Reagents

15.3.1. MONOCLONAL ANTIBODIES

Mouse monoclonal antibodies were generated according to procedure as described (Rubin, L. A., et al., 1985, Hybridoma 4:91–102; Kohler, G. and Milstein, C., 1975, Nature 256:495–497). The two monoclonal antibodies selected (2R12, 7G7) are directed against different epitopes of IL2R. Both antibodies were shown to precipitate a 55 kilodalton (kd) cell surface protein identified by anti-Tac mAb. The IgG antibodies were purified to greater than 95% homogeneity by chromatography on immobilized protein A (BioRad) according to the manufacturer's instruction (Affi-gel protein A MAPS II kit instruction manual, BioRad Laboratories, California). Enzyme-antibody conjugates were prepared by labeling IgG with horseradish peroxidase essentially as described (Wilson, M. B. and Nakane, P. K., 1978, Immunofluorescence and Related Staining Techniques, Knapp, W., K. Holubar, and G. Wicheds, eds., Elsevier/North-Holland Biomedical Press, p. 215).

15 3 2. STANDARDS

IL2R standards were prepared from supernatants of phytohemagglutinin (PHA) stimulated peripheral blood mononuclear cell (PBMC) cultures. Lymphocytes were harvested after centrifugation over Ficoll-Paque (Pharmacia) according to the manufacturer's instructions. $10^6$ cells/ml were suspended in RPMI 1640 supplemented with 100 U/ml penicillin, 100 ug/ml streptomycin and 15% fetal bovine serum. PHA (Wellcome Diagnostics) was added to a concentration of 2.0 ug/ml. Cultures were maintained at 37° C. for 3–6 days. Supernatants were harvested by centrifugation at 200×g for 8 minutes, and clarified by spinning at 10,000×g for 10 minutes. IL2R levels were assigned a value in Units per ml (U/ml) based on activity in the enzyme immunoassay relative to a reference preparation of supernatant which was arbitrarily assigned a value of 1000 U/ml (Rubin, L. A., et al., 1985, J. Immunol. 135:3172–3177).

15.3.3. PATIENT SERA

Normal sera were collected from healthy blood donors and stored at 4° C. for up to 7 days and frozen at −70° C. for longer periods of time.

Adult T cell leukemia patient sera were provided by Dr. N. Yasudo (Kyoto University, Japan). Abnormal clinical sera samples were obtained from area hospitals and clinics.

15.3.4. PURIFIED IL2R

Purified IL2R was prepared by affinity chromatography of supernatant from PHA-stimulated PBMC cultures over an anti-IL2R immunoadsorbant. The affinity column was prepared by coupling 1 mg anti-IL2R antibody (2R12) to 1 ml Reactigel (Pierce) according to the manufacturer's instructions. 100 ml of PHA supernatant culture was applied to a 1 ml column. After washing the unbound material from the gel with 100 ml of phosphate-buffered saline (PBS), the IL2R was eluted in 5 ml of 0.2M glycine buffer, pH 2.8; dialyzed in water; lyophilized and resuspended in 0.5 ml PBS.

15.3.5. INTERLEUKIN-2

A commercially available recombinant IL-2, was the generous gift of Dr. James Kurnick (Massachusetts General Hospital, Boston, Mass.).

15.4. CELLFREE ™ IL2R Assay

The CELLFREE ™ Interleukin-2 Receptor Test Kit was used for all serum assays as follows: Wells of polystyrene microstrips were coated with antibody by incubation with 100 ul per well of a 1.5 ug/ml solution of anti-IL2R mouse mAb in PBS overnight at room temperature. Coating solution was discarded and wells were blocked for 2 hours at 37° C. with 300 ul of 1.0% bovine serum albumin, 0.05% Tween 20 in PBS. Wells were then washed 3 times with washing buffer (0.05% Tween 20 in PBS). The precoated microstrips were used in either a two-step assay by an improved shorter one-step procedure. For the two-step assay, 50 ul of sample, standard, or control was placed in each well. 100 ul of sample diluent, consisting of animal serum proteins and surfactant, was added to each well. Wells were incubated for 2 hours at 37° C., the washed 3 times with washing buffer. 100 ul of HRP-conjugated anti-IL2R antibody directed against a second epitope on the IL-2 receptor was added to each well and incubated for 2 hours at 37° C. After washing the wells 3 times with washing buffer, 100 ul of substrate solution (0.2% o-phenylenediamine [OPD], 0.0225% $H_2O_2$, 65 mM dibasic sodium phosphate, 17 mM citric acid) was added per well. Wells were incubated for 30 minutes at room temperature. The reaction was stopped by the addition of 50 ul of 2 N $H_2SO_2$ to each well, and the absorbance of the wells at 490 nm was read using a Dynatech MR60 microtiter plate reader. All assay buffers and diluents contained 0.01% thimerosal as a preservative. Unknown samples were assigned values based on a standard curve constructed using standards which contained 0, 100, 400, and 160 U/ml IL2R.

Alternatively, a faster one-step method was used as follows: 50 ul of standard, sample, or control was added to each well, followed by 100 ul of HRP-conjugated antibody. Wells were incubated for 2 hours at room temperature on a shaker platform at 150–180 rpm. After washing the well three times with washing buffer, 100 ul of substrate solution was added. Wells were incubated for 20 minutes at room temperature. The reaction was stopped by adding 100 ul of 2 N sulfuric acid to each well. The absorbance was read and analyzed as described above.

15.4.1. Standardization

Figure 13:
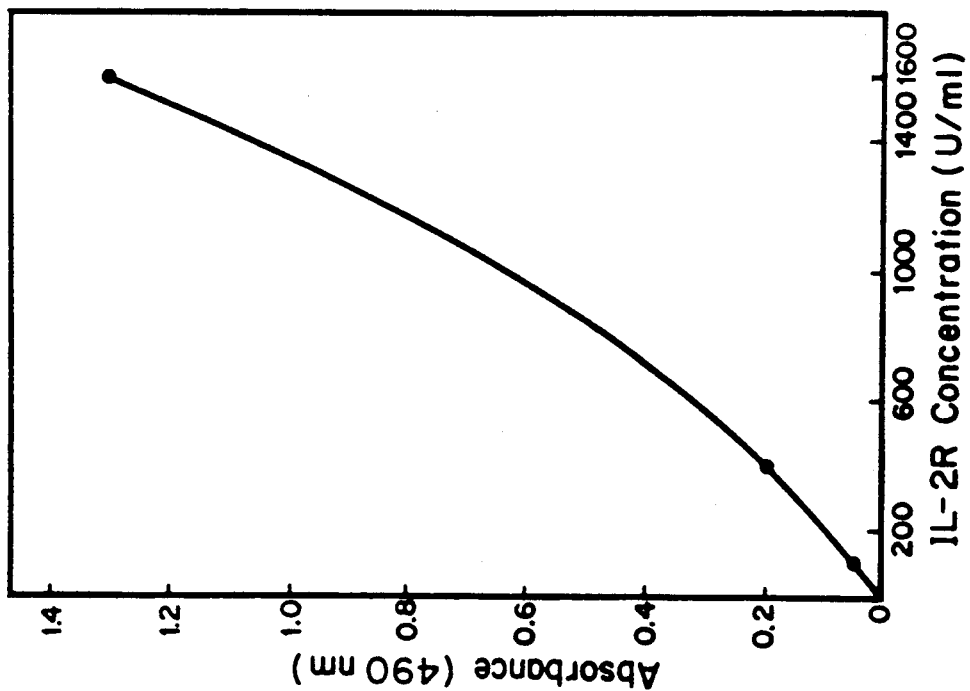

A typical standard curve is shown in FIG. 13. The sensitivity of the assay is calculated as the amount of IL2R giving two standard deviations above the absorbance of the zero standard and is approximately 50 U/ml. Samples with up to 1600 U/ml IL2R activity can be measured in the kit; greater levels can be quantitated if the sample is diluted prior to assay.

15.4 2 . Precision

Intra and inter-assay precision are presented in Table X. Intra-assay variation was determined for three serum pools with differing IL2R levels by testing 20 replicate samples of each pool in one assay run. The coefficient of variation (CV) ranged from 3.2 to 3.9%. Inter-assay variation was determined from the average of duplicate samples for 20 separate runs. The inter-assay CV ranged from 10 to 12% for the three serum pools tested.

TABLE X

| PRECISION MEASUREMENT OF THE IL2R ASSAY | | | |
|---|---|---|---|
| Sample | Mean (U/ml) | Standard Deviation (U/ml) | Coefficient of Variation (%) |
| INTRA-ASSAY PRECISION[a]: | | | |
| Serum Pool A | 386 | 14 | 3.7 |
| Serum Pool B | 636 | 25 | 3.9 |
| Serum Pool C | 1,029 | 33 | 3.2 |
| INTER-ASSAY PRECISION[b]: | | | |
| Serum Pool A | 414 | 50 | 12 |
| Serum Pool B | 688 | 73 | 11 |
| Serum Pool C | 1,109 | 107 | 10 |

[a]Intra-assay precision was determined from the mean of 20 assays per sample.
[b]Inter-assay precision was determined from the mean of the average of duplicate samples for 20 different runs.

5.4.3. Accuracy

Affinity-purified IL2R was added to normal human serum which had been stripped of endogenous IL2R by passage over an anti-IL2R affinity gel. Spiked samples with different levels of added IL2R were tested in the assay for IL2R. Recovery of IL2R was 95–103% of the expected result (Table XI).

TABLE XI

| ACCURACY OF THE IL2R ASSAY[a] | | |
|---|---|---|
| Expected Value (U/ml) | Recovered Value (U/ml) | Recovery (%) |
| 150 | 145 | 97 |
| 300 | 310 | 103 |
| 600 | 570 | 95 |
| 1200 | 1160 | 97 |

[a]Spiked samples were prepared by adding varying amounts of purified IL2R to a serum pool which had been stripped of endogenous IL2R.

15.4.4. Specificity of Assay and Effects of Interleukin-2

Both antibodies used in the immunoassay have been shown to recognize the same molecule as anti-Tac, an antibody previously shown to be specific for human IL2R (Uchiyama, T., et al., 1981, J. Immunol. 126: 1393–1397). Immunoprecipitations of $^{125}$I-labeled surface proteins from phytohemagglutinin-stimulated lymphocytes, using these antibodies, reveal a diffuse 55 kd band, and sequential immunoprecipitations demonstrate that this molecule is identical to that precipitated by anti-Tac (Rubin, L. A., et al., 1985, Hybridoma 4:91–102). Thus, one of the antibodies (2R12) demonstrates competitive binding with anti-Tac in cytofluorometric analysis of activated lymphocytes. The enzyme immunoassay employing these antibodies detects a released form of IL2R in the culture supernatants of IL2R surface positive cells (Rubin, L. A., et al., 1985, J. Immunol 135:3172–3177) and in the culture supernatant of mouse L cells transfected with a truncated form of the IL2R gene, but not in the supernatants of their normal counterparts (Treiger, B. F., et al., 1986, J. Immunol. 136:4099-4105).

Figure 14:
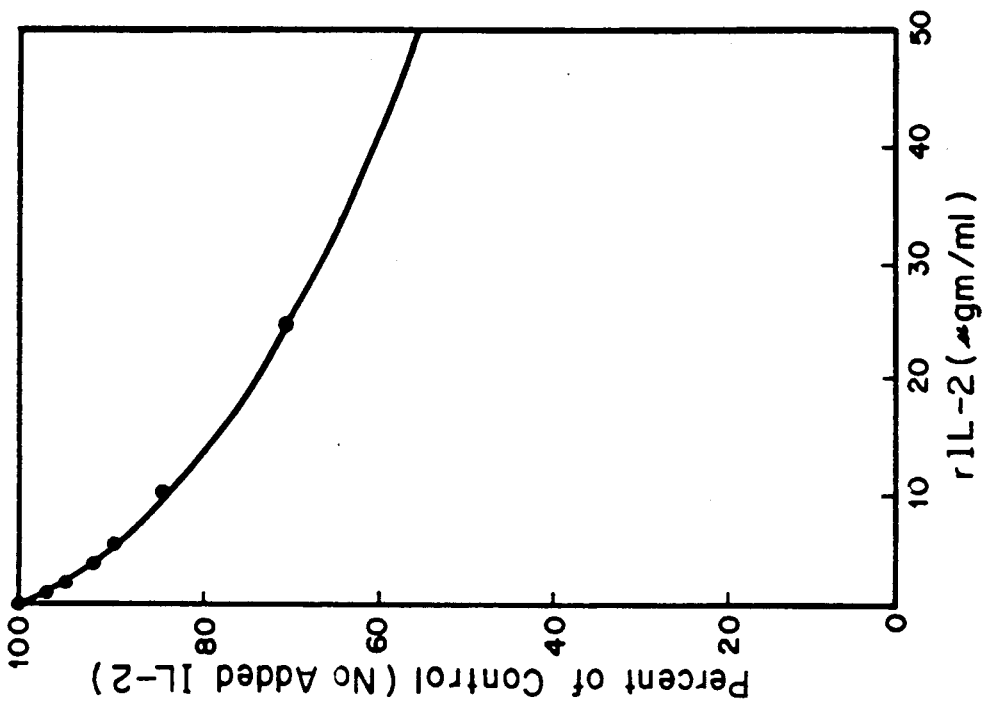

The performance of the IL2R assay kit in the presence of added IL-2 was determined. Serum concentrations of added recombinant IL-2 (rIL-2) up to 5 ug/ml caused negligible interference in IL2R detection (FIG. 14). At 500 ug/ml of added rIL-2, the IL2R level was only 40% of the expected value. The IL-2 concentrations suggested for therapeutic trials are in the 10 ug/ml range and have a half life of less than 10 minutes in serum after initial injection (Lotze, M. T., et al., 1985, J. Immunol. 135:2865-2875). Therefore, therapeutic levels of IL-2 are not expected to cause significant interference in measurement of IL2R by this assay. Greater than 80% of the expected IL2R value was obtained at these concentrations of rIL-2. In addition, no detectable level of IL-2 in normal serum was observed.

15.4.5. IIL2R Levels in Human Sera

The distribution of IL2R levels in normal human sera is presented in FIG. 14. The mean IL2R level of 174 healthy blood donors was 273 U/ml. The upper limit of normal for this group was 477 U/ml (mean+2 S.D.).

Figure 15:
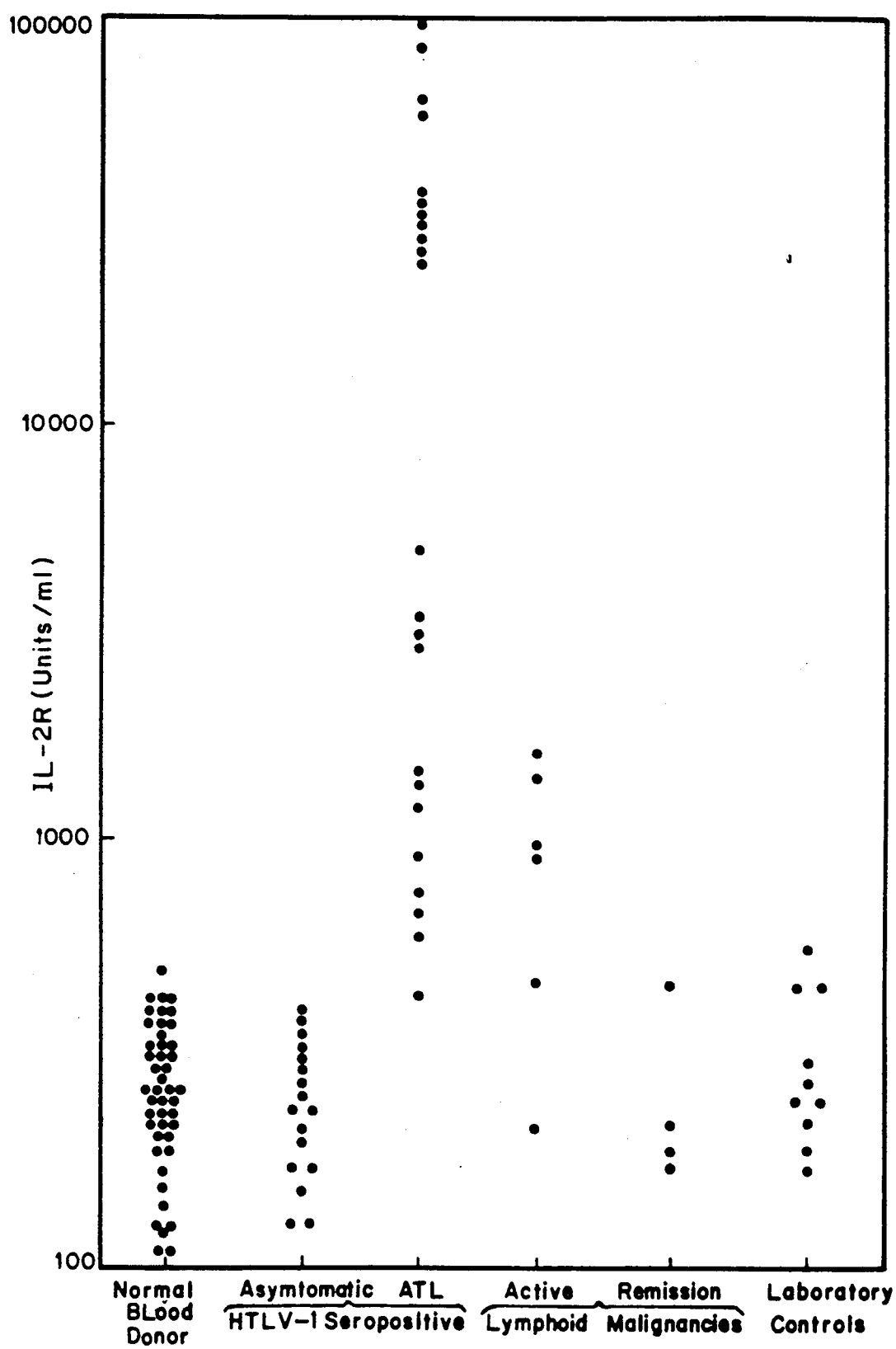

Serum IL2R levels for 22 of 23 patients with adult T cell leukemia were elevated above the normal level (FIG. 15). The majority of these patients had marked elevations of IL2R level (greater than 1600 U/ml).

The current test demonstrates a detectable level of released IL2R present in normal human sera and increased serum levels of IL2R in adult T cell leukemia patients (Rubin, L. A., et al., 1986, "Identification and Characterization of a Released Form of the Interleukin-2 Receptor, in Leukocytes and Host Defense, Oppenheim, J. J. and D. M. Jacobs, eds., Alan R. Liss, Inc., New York, pp. 95-102).

As an alternative to cell surface measurements, the availability of a commercial enzyme immunoassay for the detection of released or soluble IL2R makes it possible to assess altered immune status in a new manner. This method can allow detection of IL2R released from sequestered as well as circulating activated cells. Invasive tissue sampling methods for obtaining compartmentalized cells is thus avoided. Furthermore, the serum IL2R assay can provide means for rapid retrospective analysis of stored serum to provide insight into immune regulation.

16. Soluble IL-1 Receptor Detection in Patient Serum

The examples described below demonstrate that elevated levels of IL-1 receptor can be detected in leukemia patient samples using the assays of the present invention.

16.1. Monoclonal Antibodies

A murine anti-IL-1 receptor mAb was generated according to standard techniques (Kung, P. C., et al., 1979, Science 206:347-349) using spleen cells from mice immunized with IL-1 receptor purified by published procedures (Muchmore, A. V. and Decker, J. M., 1985, Science 229:479-481). Rabbit polyclonal antibody (hetero-serum) directed against the IL-1 receptor was generated by immunizing a rabbit with purified uromodulin as previously described (id.)

16.2. Soluble IL-1 Receptor Assay

Soluble IL-1 receptor was detected in samples using the procedure outlined below:

(a) Polystyrene microtiter wells (Flow Laboratory) were coated overnight at 4° C. with 100 ul of a murine anti-IL-1 receptor monoclonal antibody (2.5 ug/ml) in PBS.

(b) Coating solution was discarded and wells were blocked for 1-2 hours at room temperature with 300 ul of 1% BSA in Tris-Tween Buffer.

(c) Wells were washed 3 times with Tris washing solution.

(d) 50 ul sample was added per well followed by 100 ul diluent containing 50% fetal calf serum in Tris-buffered saline and 0.1% NP-40. Wells were incubated 2 hours at 37° C.

(e) Wells were washed 3 times with Tris washing solution.

(f) 100 ul of rabbit anti-IL-1 receptor polyclonal antibody (hetero-serum) was added at a titrated dilution of 1/1000 with Tris-buffered saline.

(g) Incubation for 2 hours at 37° C.

(h) Wells were washed 3 times with Tris washing solution.

(i) 100 ul of goat anti-rabbit IgG, horseradish peroxidase conjugate (Tago, Calif.) at 1/2000 dilution was added to each well.

(j) Incubation for 1 hour at 37° C.

(k) Wells were washed 4 times with Tris washing solution.

(l) 100 ul of 0.2% o-phenylenediamine (OPD) and 0.015% of $H_2O_2$ in citrate-phosphate buffer was added per well. Plates were incubated for 30 minutes at room temperature.

(m) 50 ul of 2 N $H_2SO_4$ was added to each well and the absorbance of each well was measured at 490 nm on a microtiter plate reader.

16.3 Results

As shown in Table XII, plasma isolated from normal healthy donors indicated low levels of soluble IL-1 receptor. However, the plasma levels of soluble IL-1 receptor were highly elevated in some leukemia patients. Urine samples obtained from patients also contained highly elevated and widely variable levels of soluble IL-1 receptor.

TABLE XII

SOLUBLE IL-1 RECEPTOR LEVEL IN PATIENT SAMPLES (OPTICAL DENSITY)

| | Plasma Samples | | |
|---|---|---|---|
| | Healthy Donor | Leukemia Patients | Urine Samples |
| 1 | 0.007 | 0.593 | 0.767 |
| 2 | 0.008 | 0.109 | 0.741 |
| 3 | 0.039 | 0.244 | 1.612 |
| 4 | 0.037 | 0.095 | 0.495 |
| 5 | 0.003 | 0.060 | 0.336 |
| 6 | 0.026 | 0.048 | 0.284 |
| 7 | 0.007 | 0.060 | 1.473 |

17 Soluble CD8 Detection in Patients

The following sections describe antibodies and assays that can be used to detect soluble CD8 in patients.

17.1. Monoclonal Antibodies

Anti-CD8 monoclonal antibody 5F4 was generated according to Reinherz et al. (1979, Proc Natl. Acad. Sci. U.S.A. 76:4061-4065) by immunizing BALB/c mice with a human T cell line (Jurkat). Monoclonal antibody 5F4 recognizes an epitope on CD8 that is different from the epitope on CD8 which is recognized by mAb OKT8.

17.2. Soluble CD8 Assay

Soluble CD8 was detected in samples using the procedure outlined below:

(a) Polystyrene microtiter wells (Flow Laboratory) were coated overnight at 4° C. with 100 ul of an anti-CD8 murine monoclonal antibody (2.5 ug/ml) of mAb OKT8 (Ortho Diagnostics, Raritan, N.J.) in PBS.

(b) Coating solution was discarded and wells were blocked for 1-2 hours at room temperature with 300 ul of 1% BSA in Tris-buffered saline containing 25 mM Tris pH 7.4 in 0.05% Tween 20 and 0.15 M sodium chloride (NaCl).

(c) Wells were washed 3 times with 10 mM Tris, 0.05% Tween 20, pH 8.0 (Tris washing solution).

(d) 10 ul sample was added per well, followed by 90 ul diluent containing 50% FCS in Tris-buffered saline and 0.4% NP-40 (Sigma). Wells were incubated 2 hours at 37° C.

(e) Wells were washed 3 times with Tris washing solution.

(f) 100 ul of horseradish peroxidase conjugated anti-CD8 murine monoclonal antibody (0.2 ug/ml mAb 5F4) in 50% FCS, 25 mM Tris pH 7.4, 0.15 M NaCl and 0.1% NP-40 was added to each well and incubated 2 hours at 37° C.

(g) Wells were washed 4 times with Tris washing solution.

(h) 100 ul of 0.2% o-phenylenediamine (OPD) and 0.015% of $H_2O_2$ in citrate-phosphate buffer was added per well. Plates were incubated for 30 minutes at room temperature.

(i) 50 ul of 2 N $H_2SO_4$ was added to each well and the absorbance of each well was measured at 490 nm in a microtiter plate reader.

17.3. CD8 Control Standards

The supernatant of a tissue culture line (Jurkatt) was used as the standard. The measured value was assigned a reference number of 2000 units/ml. The culture supernatant consisted of RPMI-1640 medium containing 10% FCS and 100 units of penicillin-streptomycin.

17.4 Enzyme Immunoassay for the Quantitation of Cell-Free Human T Cell CD8-Like Molecule Using two monoclonal antibodies directed against distinct epitopes on the CD8 antigen, a human suppressor/cytotoxic T cell marker, we have developed a sensitive quantitative enzyme immunoassay for measuring the cell free form of a human T cell CD8-like antigen. Elevated levels of this antigen are observed in a number of diseases and conditions including certain leukemias, allograft transplantation, and autoimmune diseases such as rheumatoid arthritis and lupus. In longitudinal patient studies, increases in the serum level of cell-free CD8 are seen in a different time frame when compared to the expression of soluble interleukin-2 receptor (IL2R). In certain instances, elevations of cell-free CD8-like molecules are preceded by several days with elevations in serum IL2R levels. Increased levels of this cell-free CD8-like molecule may indicate the involvement of significant numbers of suppressor/cytotoxic T cells with a specific pathological event, distinct from immune activation as measured by a rise in cell-free IL2R. The presence of cell-bound CD8 and IL2R molecules is typically measured by cell surface staining. These cell-free assays may provide a more thorough understanding of certain immunological disorders.

The assay used for CD8 was a sandwich enzyme immuno-assay, as described in Section 17.2, supra. An anti-CD8 mAb (mAb 1) was coated onto a solid substratum, e.g. microtiter wells. CD8 in the sample binds to the antibody-coated well; unreacted sample components are washed away. An enzyme-conjugated, second anti-CD8 mAb (mAb 2), recognizing a different epitope than that of mAb 1, binds to the CD8 antigen captured by the first antibody and completes the sandwich. Unbound mAb 2 was removed by washing. A substrate solution was added to the wells, and a colored product formed in proportion to the amount of CD8 present in the sample. The reaction was terminated by stop solution and the absorbance was measured. A standard curve is prepared from CD8 standards (See Section 17.3, supra). Unknown values were determined from the standard curve.

17.4.1. Evaluation of Anti-CD8 Monoclonal Antibodies as a Capture Antibody

Various monoclonal antibodies (mAbs) directed against the CD8 antigen were tested for their suitability as a capture antibody in an enzyme immunoassay employing anti-CD8 mAb 5F4 as detection antibody (mAb 2).

Plates (Flow microstrips, Flow Laboratory, McClean, Va.) were coated overnight with 2.5 ug/ml of capture antibody. Non-reactive sites were blocked the next day with a solution containing 1% BSA in 0.15 M NaCl, 0.025 M Tris-Cl (pH 7.4), 0.01% thimerosal, 0.05% Tween 20. 100 ul sample was added, consisting of CD8-containing Jurkat cell supernatant, diluted 1:4 in 25% fetal calf serum, 0.25% Nonidet P-40 (NP-40) in Tris-buffered saline. After incubation for 90 minutes at 37° C., the plates were washed with 10 mM Tris, 0.05% Tween 20, pH 8.0. 100 ul of horseradish peroxidase (HRP)-conjugated mAb 5F4 (at 1:5000 dilution of a 1 mg/ml stock) in 25% fetal calf serum, 0.25% NP-40 in Tris-buffered saline was added. Plates were incubated for 90 minutes at 37° C. and washed as above. 100 ul of 0.2% o-phenylenediamine was added in 0.015% $H_2O_2$, and incubated for 30 minutes at room temperature, after which absorbance was read at 450 nm. Results are as shown in Table XIII.

TABLE XIII

| EVALUATION OF ANTI-CD8 MONOCLONAR ANTIBODIES AS A CAPTURE ANTIBODY[1] | | |
|---|---|---|
| Capture Antibody | Ability to Compete Binding of mAb 5F4 to CD8 | $OD_{450}$[2] |
| B98.1.1 | Partial | 0.028 |
| B116.1.1 | Yes | 0.027 |
| B99.1.1 | No | 0.039 |
| OKT8 | No | 0.413 |
| 4C9 | No | 1.106 |
| 5F4 | Yes | 0.042 |
| 62EC[3] (control) | Yes | 0.042 |

[1] With conjugated mAb 5F4 as detection antibody
[2] Readings at or below 0.042 (negative control) are considered negative
[3] Negative control mAb, directed against Keyhole limpet hemocyanin (Pacific Biolabs, CA)

The results of binding competition assays to mAb 5F4 are also shown in Table XIII. These assays were carried out using the same protocol described supra, except that the capture antibody was OKT8 and the detection antibody was a mixture of 50 ul competing antibody (1 ug/ml) plus 50 ul HRP-conjugated mAb 5F4 (at 1:2500 dilution of a 1 mg/ml stock).

As shown in Table XIII, the seven mAbs tested as capture antibodies can be classified into three groups, based on their ability to competitively inhibit binding of mAb 5F4 to CD8 antigen. As expected, use of the 5F4 mAb as both capture and detection antibody does not work (since capture antibody 5F4 competes out detection antibody 5F4 binding). Surprisingly, among the group of mAbs which did not competitively inhibit binding of 5F4 to CD8, 4C9 worked best, giving the highest assay results, followed by OKT8, whereas B99.1.1 was negative. Thus, it is not obvious, even based upon competition ability, to predict which anti-CD8 monoclonal antibodies will work in a sandwich immunoassay.

A comparison of the serum CD8 levels measured by use of mAb OKT8 versus mAb 4C9 as capture antibody was also done. mAb 5F4 was used as a detection antibody. The results, shown in Table XIV, demonstrate a greater CD8 detection level using 4C9 as capture antibody in the vast majority of cases.

TABLE XIV

COMPARISON OF CD8 LEVELS USING 2 DIFFERENT ANTI-CD8 CAPTURE ANTIBODIES[1]

| | U/ml | |
|---|---|---|
| | MEASURED USING OKT8 CAPTURE | MEASURED USING 4C9 CAPTURE |
| PATIENT GROUP | 96 | 143 |
| NORMAL | 122 | 207 |
| | 211 | 211 |
| | 52 | 72 |
| | 146 | 209 |
| | 59 | 147 |
| | 20 | 72 |
| | 14 | 65 |
| | 76 | 270 |
| | 33 | 270 |
| | 52 | 261 |
| | 76 | 329 |
| | 63 | 394 |
| | 193 | 724 |
| | 14 | 96 |
| | 91 | 252 |
| | 33 | 188 |
| | 269 | 858 |
| | 57 | 292 |
| | 22 | 226 |
| RENAL TRANSPLANT | 237 | 721 |
| PATIENTS | 229 | 620 |
| | 393 | 1249 |
| | 303 | 687 |
| | 231 | 613 |
| | 488 | 1464 |
| | 824 | 1665 |
| | 351 | 1176 |
| | 381 | 1603 |
| | 432 | 1002 |
| | 202 | 171 |
| | 198 | 131 |
| | 455 | 248 |
| | 502 | 361 |
| | 98 | 110 |
| | 133 | 190 |
| | 324 | 377 |
| | 144 | 319 |

[1]With anti-CD8 mAb 5F4 as detection antibody

18. Serum CD8 Levels in Evaluation of Diseases and Disorders

A number of diseases and disorders can be staged or diagnosed by measuring serum CD8 levels in patients. Examples are described in the subsections below.

18.1 Differential Diagnosis of Rheumatoid Arthritis

Figure 16:
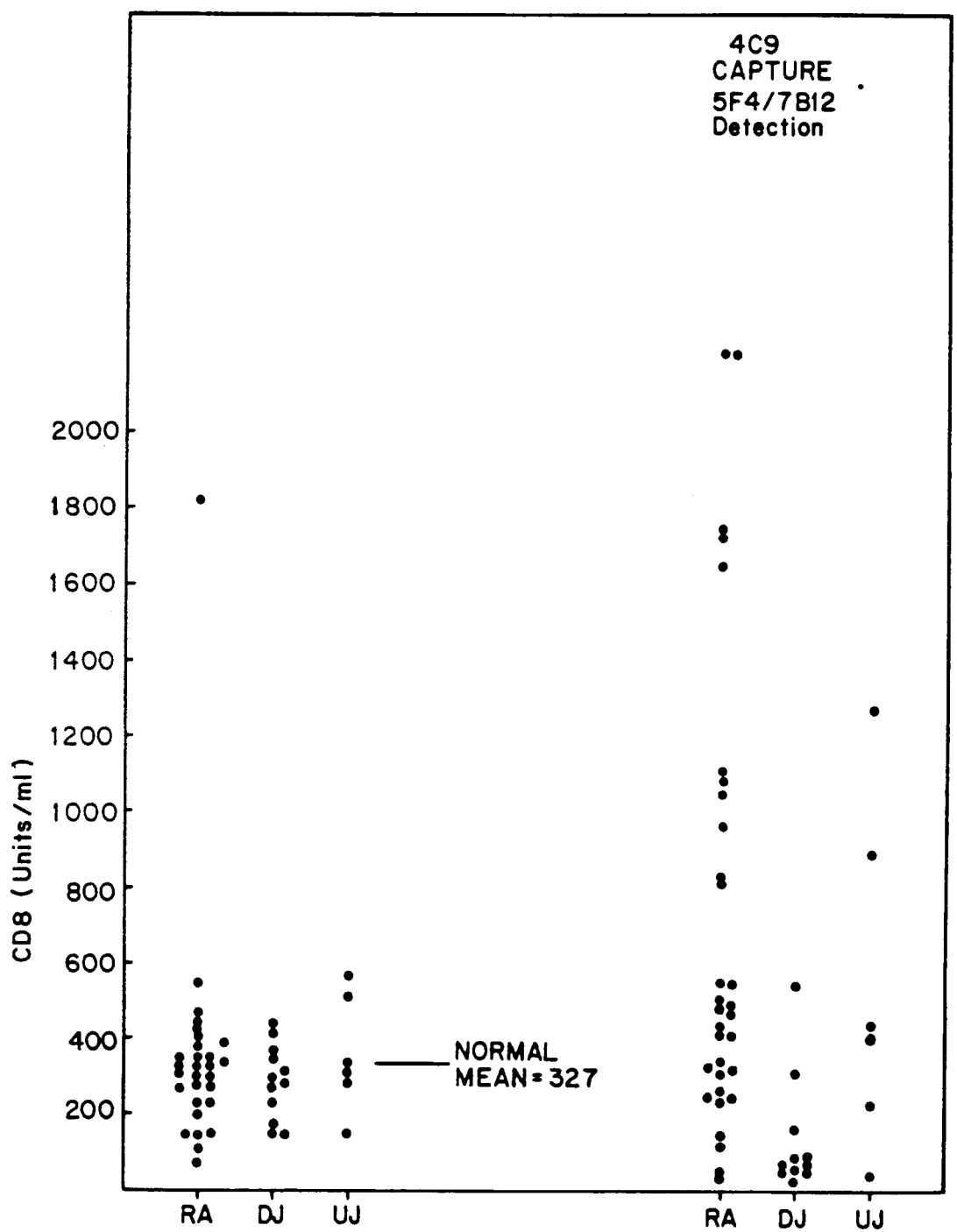

Using the CD8 sandwich enzyme immunoassay described above one can distinguish rheumatoid arthritis from other joint diseases (FIG. 16). The results shown in FIG. 16 are based on the level of serum or synovial fluid CD8 concentration, measured using mAb 4C9 as capture antibody, and mAb 5F4 as detection antibody.

18.2 Serum CD8 Levels in a Renal Allograft Recipient

Patient A was the recipient of a HLA nonidentical renal allograft from cadaver. The patient was transplanted on May 23, and maintained on cyclosporin A (CsA). From May 23 through May 31, the patient experienced CsA toxicity and some early rejection. On June 28, a rejection episode was diagnosed (based on a rise in creatinine level, and the patient was administered OKT3 mAb, at 5 mg doses intravenously four times a day, through July 7. On July 8, the creatinine level had decreased, and the patient had entered the process of recovery. On July 18, there was another rise in creatinine level that was treated by administration of prednisone, which resulted in a decrease in the creatinine level until August 26, at which time another dose of prednisone was administered.

Figure 17:
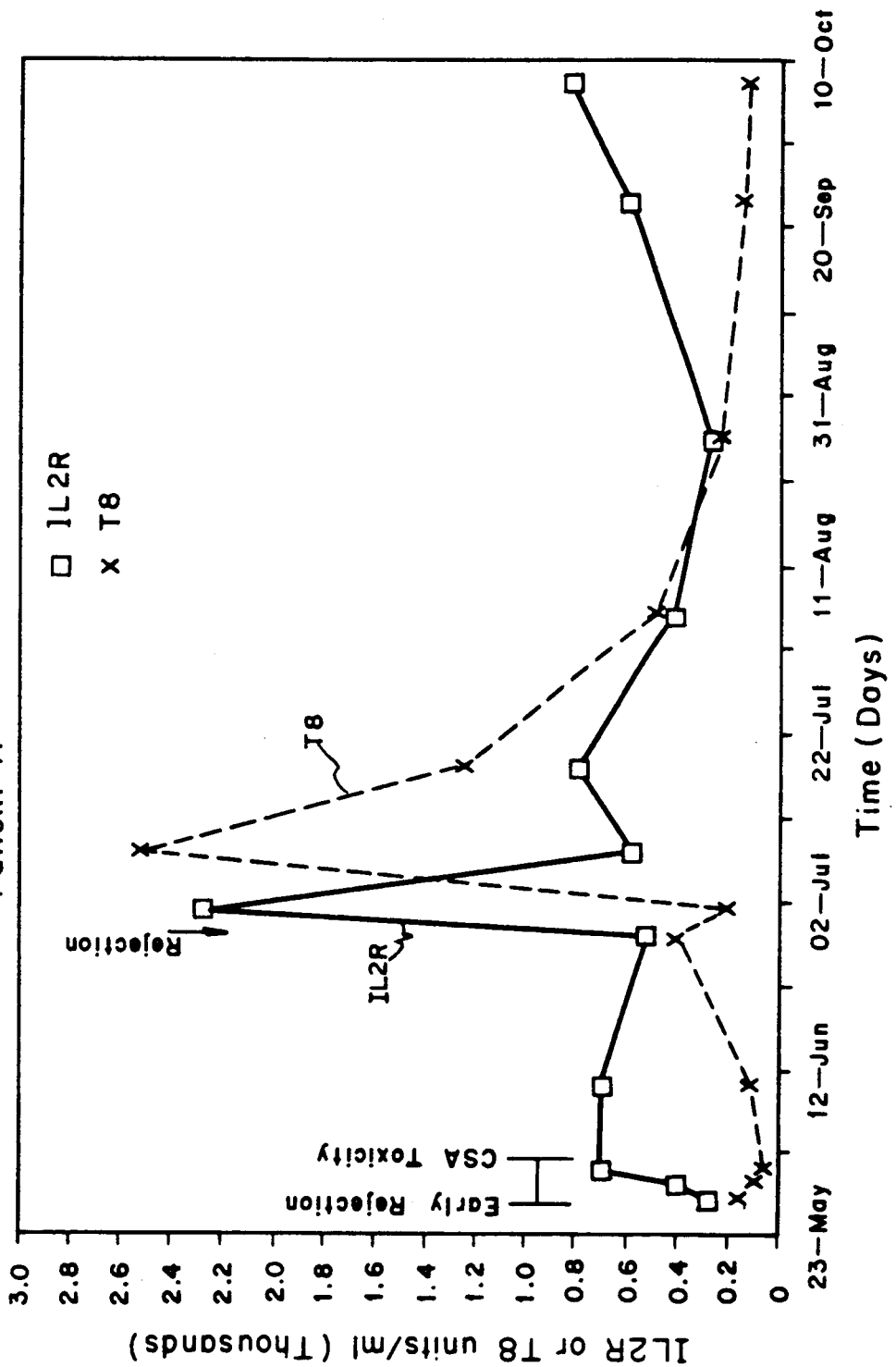

IL2R and CD8 levels in the patient serum were measured at suitable intervals from May 23 (transplant date) on, and are shown in FIG. 17 which shows a peak in serum CD8 levels after a rejection episode (but not after an episode of CsA toxicity). This is suggestive of a role for measurement of serum CD8 levels in the monitoring and differential diagnosis of renal transplant.

18.3 Serum CD8 Levels in Children with Non-Hodgkin's Lymphoma

CD8 levels were measured in the serum of the children with non-Hodgkin's lymphoma (NHL) or B-cell acute lymphoblastic leukemia (ALL), that were used in the study of IL2R serum levels, described in Section 9, supra.

Figure 18:
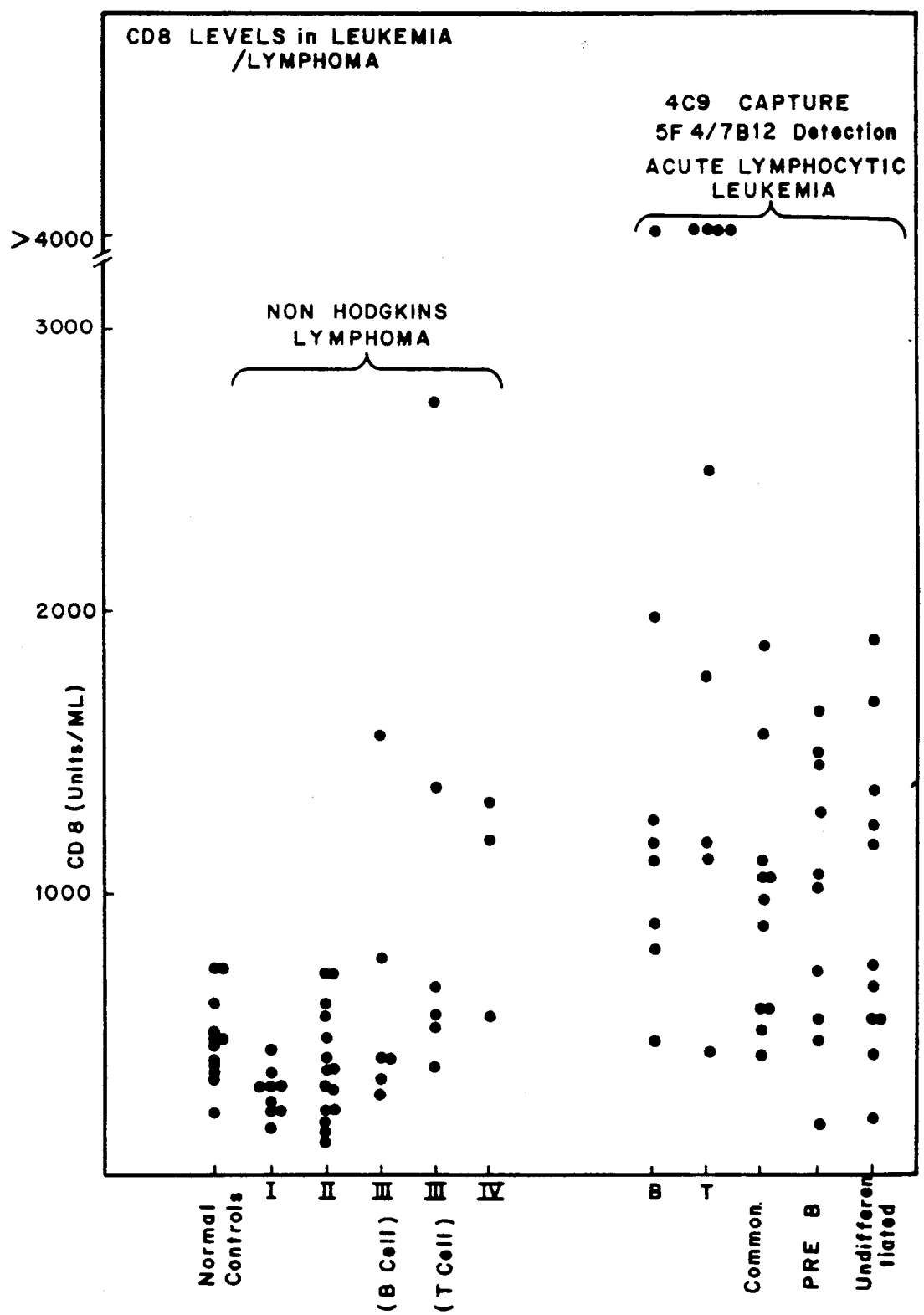

The enzyme sandwich immunoassay, described above was used, with anti-CD8 mAbs 4C9 and 5F4 as the capture and detection antibodies, respectively. The results shown in FIG. 18 demonstrate that a detectable increase in the level of serum CD8 antigen in patients appears to be related to advanced disease and a poor outcome.

18.4. CD8 Levels in Infectious Disease

Figure 19:
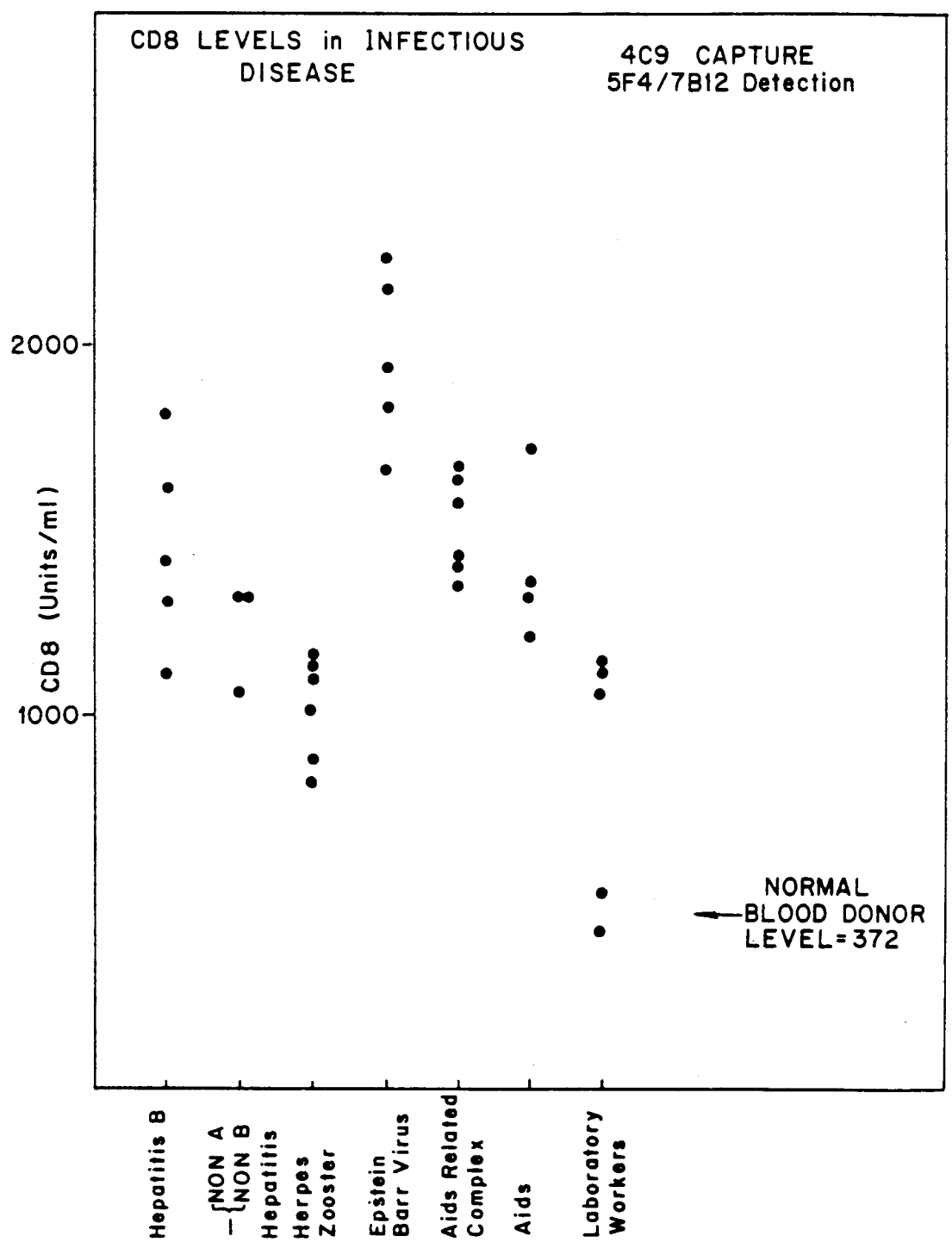

The enzyme sandwich immunoassay, as described in Section 17.2., was used to measure CD8 levels in the serum of patients with an infectious disease. Anti-CD8 mAbs 4C9 and 5F4 were used as the capture and detection antibodies, respectively. The results, shown in FIG. 19, demonstrate an elevated level of the CD8 antigen, particularly in patients with Hepatitis B, Epstein Barr virus, AIDS related complex, and AIDS disorders.

19. Molecular Characterization of the Soluble CD8 Antigen

Jurkat cell supernatants and cell lysates were immunoprecipitated with anti-CD8 mAbs, in order to study the molecular nature of the CD8 antigen in its soluble and cell-associated forms that is recognized by the antibodies.

19.1 Methods $5 \times 10^6$ Jurkat cells in a Falcon T25 flask were pulse-labeled with 2 mCi $^{35}$S-methionine in met$^-$ RPMI 1640 medium. After six hours, the media was removed, cells were washed with the complete RPMI 1640 media, and cells were incubated in complete RPMI 1640 media for 16 hours before harvesting. Cells were pelleted by centrifugation. Supernatant samples were prepared by centrifuging cell culture supernatant at 20,000×g for 30 minutes, and filtering the supernatant through a 0.22 um Millipore TM filter. Cell lysates were prepared by resuspending $5 \times 10^6$ cells in 1 ml lysis buffer: 0.15 M NaCl, 25 mM Tris-Cl (pH 8.0), 1 mM MgCl$_2$, 1% Nonidet P-40 (NP-40, polyoxyethylene (9) p-tert-octylphenol), 1 mM phenylmethylsulfonylfluoride (PMSF), 0.2 mg/ml alpha-2-macroglobulin, 10 mM iodoacetamide, 0.1 mg/ml ovomucoid trypsin inhibitor. Cells plus lysis buffer were allowed to stand for 0.5 hour at 4° C., centrifuged at 20,000×g for 30 minutes, and the supernatant (cell lysate sample) removed for immunoprecipitation.

Culture supernatants and cell lysates were purified by immunoprecipitating with anti-CD8 mAbs 5F4, 4C9, and OKT8. The immunoprecipitation was accomplished in two steps: a nonspecific adsorption step, and a specific binding step. To remove non-specifically bound material, the lysate or cell supernatant sample was incubated with 5% volume of packed Sepharose coupled to mouse immunoglobulin G (Affigel, Biorad, Richmond, Calif.) for 3 hours on a rocker at room temperature. After spinning out the Sepharose, the supernatant (either 1 ml culture supernatant sample or 0.2 ml lysate sample) was incubated with 10 ul packed Sepharose coupled to either mAb OKT8 or 4C9 or 5F4, or control mAb OKT3. Samples were agitated at room temperature for two hours, and then washed ten times with 1.5 ml phosphate-buffered saline. Samples were eluted into 200 ul 50 mM diethylamine, 0.15 M NaCl, pH 11.0. The eluate was diluted with an equal volume of electrophoresis sample buffer. One-half of each eluate was then reduced by addition of dithiothreitol (DTT) to a concentration of 10 mM; one-half of each eluate was left unreduced. Samples were boiled and loaded onto a 10-20% sodium dodecyl sulfate-polyacrylamide gel. Gels were dried and exposed for autoradiography.

19.2. Anti-CD8 mAbs -Recognize a Soluble CD8 Antigen of 52-55 Kilodaltons

The nonreduced cell lysate immunoprecipitates contained predominantly a 52-55 kd form. This is somewhat smaller than the 66 Kd cell surface form of the CD8 antigen previously reported (Fujimoto, J., et al., 1983, J. Exp. Med. 159: 752-766). Surprisingly, the nonreduced cell culture supernatant immunoprecipitate contained only the 52-55 kd dimeric form of the CD8.antigen. This is in contrast to the results of Fujimoto et al., who detected only a 27 kd monomer form under either reducing or nonreducing conditions, of the soluble CD8 antigen in sandwich immunoassays (Fujimoto et al., supra). In the reduced supernatant immunoprecipitate described herein, the 27 kd CD8 monomer was observed, confirming the identity of the 52-55 kd soluble form as a homodimer. Thus, the anti-CD8 mAbs recognized a dimeric 52-55 kd form of the CD8 antigen as both a soluble and a cell-associated molecule.

When a reducing agent, DTT, was included in a sandwich enzyme immunoassay for CD8 antigen in supernatant samples, no binding was observed. Thus, reduction of the soluble dimeric form to monomer abolished the ability of the anti-CD8 mAbs to bind the soluble antigen, confirming that these anti-CD8 mAbs may bind only to a soluble CD8 dimer.

20. Soluble CD2 Detection

The supernatants of various cultured cells were assayed for soluble CD2 using two monoclonal antibodies which define different epitopes of the CD2 (T11) molecule. Samples were assayed using a sandwich immunoassay format as previously described, in which monoclonal antibodies B67.6.1.1 and B67.1.1.1. (Perussia, B , et al., 1983, J. Immunol. 130:2142) were used as the capture and detection antibodies, respectively, and vice versa.

A released form of CD2 was detected in supernatants of the following cultured cells which are CD2 surface positive: HPB-ALL, Jurkat, CEM and MOLT-4. By contrast, soluble CD2 was not detected in the supernatants of cultured cells which are CD2 surface negative such as DAUDI. Soluble CD2 was also not detected in the supernatant of cultured PEER cells, a T cell line which is weakly CD2 surface positive.

21. Deposit Of Hybridomas

The following hybridoma cell lines, producing the indicated monoclonal antibody, have been deposited with the American Type Culture Collection, Rockville, Md., and have been assigned the listed accession numbers:

| Hybridoma | Monoclonal Antibody | Accession Number |
|---|---|---|
| Cell line AM92/2R12 | AM92/2R12 (anti-IL2R) | HB 9341 |
| Cell line 7G7 | 7G7 (anti-IL2R) | HB 8784 |
| Cell Line 4C9 | 4C9 (anti-CD8) | HB 9340 |
| Cell line 5F4/7B12 | 5F4/7B12 (anti-CD8) | HB 9342 |

The present invention is not to be limited in scope by the cell lines deposited since the deposited embodiment is intended as a single illustration of one aspect of the invention and any cell lines which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

What is claimed:

1. A method for detecting an advanced stage of a lymphatic malignancy, comprising measuring the concentration of soluble interleukin-2 receptor in a body fluid obtained from a patient with the lymphatic malignancy, in which the concentrated of soluble interleukin-2 receptor is indicative of the stage of malignancy.

2. A method for monitoring the effect of a therapeutic treatment on a patient with a lymphatic malignancy comprising measuring the concentration of soluble interleukin-2 receptor in a body fluid obtained from the patient, in which elevated levels of the soluble interleukin-2 receptor relative to those levels present in normal individuals indicate a poor response to therapy.

3. The method according to claim 1 or 2 in which the lymphatic malignancy comprises non-Hodgkins lymphoma.

4. The method according to claim 1 or 2 in which the lymphatic malignancy comprises leukemia.

5. A method for monitoring the effect of interleukin-2 therapy on a patient with a non-lymphatic malignancy comprising, measuring the concentration of soluble interleukin-2 receptor in a body fluid obtained from the patient receiving interleukin-2 therapy, in which elevated levels of the soluble interleukin-2 receptor relative to those levels present in normal individuals or in the patient prior to the therapy indicate a positive response to the interleukin-2 therapy.

6. The method according to claim 5 in which the non-lymphatic malignancy comprises lung carcinoma.

7. A method for monitoring viral infection in a patient comprising measuring the amount of soluble interleukin-2 receptor in a body fluid obtained from the patient in which an elevated level of soluble interleukin-2 receptor relative to those levels present in normal individuals or in the patient at an earlier time indicates active viral infection.

8. The method according to claim 7 in which the virus comprises HTLV-III.

9. A method for detecting a cell free soluble CD8 T cell antigen in a sample comprising:
 (a) contacting the sample with a first monoclonal anti-CD8 antibody and with a second monoclonal anti-CD8 antibody that does not compete for the same binding site as the first anti-CD8 antibody under conditions which allow immunospecific binding; and
 (b) detecting whether immunospecific binding occurs of a component in the sample with both first and second anti-CD8 antibodies, in which immunospecific binding of a component of the sample by both first and second anti-CD8 antibodies indicates the presence of the cell free soluble CD8 in the sample,
in which the first antibody comprises 4C9, ATCC accession number HB 9340, and the second antibody comprises 5F4/7B12, ATCC accession number HB 9342.

10. A method for detecting a cell free soluble CD8 T cell antigen in a sample comprising:
 (a) contacting the sample with a first monoclonal anti-CD8 antibody and with a second monoclonal anti-CD8 antibody that does not compete for the same binding site as the first anti-CD8 antibody under conditions which allow immunospecific binding; and
 (b) detecting whether immunospecific binding occurs of a component in the sample with both first and second anti-CD8 antibodies, in which immunospecific binding of a component of the sample by both first and second anti-CD8 antibodies indicates the presence of the cell free soluble CD8,
in which the first anti-CD8 antibody is immobilized and the second anti-CD8 antibody is labeled so that immunospecific binding is indicated by the detection of immobilized label, and in which the immobilized antibody comprises 4C9, ATCC accession number HB 9340, and the labeled antibody comprises 5F4/7B12, ATCC accession number HB 9342.

11. A method for staging a lymphatic malignancy, comprising measuring the concentration of soluble CD8 in a body fluid obtained from a patient with the lymphatic malignancy, in which the concentration of soluble CD8 is indicative of the stage of the malignancy, and in which the soluble CD8 is a dimer having a molecular weight of 52–55 kilodaltons as determined by polyacrylamide gel electrophoresis.

12. A method for monitoring the effect of a therapeutic treatment on a patient with a lymphatic malignancy comprising measuring the concentration of soluble CD8 in a body fluid obtained from the patient, in which elevated levels of the soluble CD8 relative to those levels present in the patient prior to the treatment indicate a poor response to therapy, and in which the soluble CD8 is a dimer having a molecular weight of 52–55 kilodaltons as determined by polyacrylamide gel electrophoresis.

13. The method according to claim 11 or 12 in which the lymphatic malignancy comprises non-Hodgkins lymphoma.

14. A method to aid in the diagnosis of rheumatoid arthritis in a patient comprising, measuring the concentration of soluble CD8 in a body fluid obtained from the patient, in which elevated levels of the soluble CD8 relative to those levels present in normal individuals or in the patient at an earlier time indicate the existence of rheumatoid arthritis as opposed to nonspecific joint disease.

15. The method according to claim 14 in which the body fluid comprises synovial fluid.

16. A method for detecting allograft rejection in a transplant patient comprising, measuring the amount of soluble CD8 in a body fluid obtained from the transplant patient in which elevated levels of soluble CD8 relative to those levels present in normal individuals or in the patient at an earlier time indicate rejection of the allograft.

17. The method according to claim 16 in which the transplant comprises a renal allograft.

18. A method for monitoring viral infection in a patient comprising measuring the amount of soluble CD8 in a body fluid obtained from the patient in which an elevated level of soluble CD8 relative to those levels present in normal individuals or in the patient at an earlier time indicates active viral infection.

19. The method according to claim 18 in which the virus comprises HTLV-III.

20. The method according to claim 18 in which the virus comprises Epstein Barr Virus.

21. The method according to claim 18 in which the virus comprises Hepatitis B virus.

22. A substantially pure, spontaneously released, cell free soluble CD8 antigen which comprises a dimer consisting of monomers each having a molecular weight of 27 kilodaltons as determined by polyacrylamide gel electrophoresis.

23. A kit for measuring the level of cell free soluble CD8 T cell antigen in a sample comprising:
  (a) a first anti-CD8 monoclonal antibody; and
  (b) a second anti-CD8 monoclonal antibody that does not compete for the same binding site on CD8 as the first anti-CD8 monoclonal antibody,
in which the first antibody comprises 4C9, as deposited with the ATCC and assigned accession number HB 9340, and the second antibody comprises 5F4/7B12, as deposited with the ATCC and assigned accession number HB 9342.

24. The kit of claim 23 in which antibody 5F4/7B12, as deposited with the ATCC and assigned accession number HB 9342, is labeled.

25. The kit of claim 24 in which the label is an enzyme.

26. The kit of claim 25 in which the enzyme is horseradish peroxidase.

27. The method according to claim 1, 2, 5 or 7 in which the body fluid comprises serum.

28. The method according to claim 1, 2, 5 or 7 in which the soluble interleukin-2 receptor is detected by:
  (a) contacting the body fluid with monoclonal antibodies 2R12, ATCC accession number HB 9341, and 7G7, ATCC accession number HB 8784, under conditions which allow immunospecific binding; and
  (b) detecting whether immunospecific binding occurs of a component in the body fluid with both monoclonal antibodies 2R12 and 7G7; in which such immunospecific binding indicates the presence of the soluble interleukin-2 receptor in the body fluid.

29. The method according to claim 28 in which the body fluid comprises serum.

30. The method according to claim 9 or 10 in which the sample comprises a body fluid.

31. The method according to claim 30 in which the body fluid comprises serum.

* * * * *